United States Patent
Aibara

(10) Patent No.: US 9,333,411 B2
(45) Date of Patent: May 10, 2016

(54) EXERCISE SUPPORTING DEVICE, EXERCISE SUPPORTING METHOD AND EXERCISE SUPPORTING PROGRAM

(71) Applicant: CASIO COMPUTER CO., LTD., Shibuya-ku, Tokyo (JP)

(72) Inventor: Takehiro Aibara, Hamura (JP)

(73) Assignee: CASIO COMPUTER CO., LTD., Tokyo (JP)

(*) Notice: Subject to any disclaimer, the term of this patent is extended or adjusted under 35 U.S.C. 154(b) by 257 days.

(21) Appl. No.: 14/011,582

(22) Filed: Aug. 27, 2013

(65) Prior Publication Data
US 2014/0067096 A1 Mar. 6, 2014

(30) Foreign Application Priority Data
Aug. 29, 2012 (JP) ................. 2012-188410

(51) Int. Cl.
*G06F 17/00* (2006.01)
*A63B 71/06* (2006.01)
(Continued)

(52) U.S. Cl.
CPC . *A63B 71/06* (2013.01); *A61B 5/11* (2013.01); *G06Q 10/0639* (2013.01); *A61B 5/1112* (2013.01); *A61B 5/681* (2013.01); *A61B 5/7275* (2013.01); *A61B 2503/10* (2013.01)

(58) Field of Classification Search
CPC ................. A63B 2024/0065; A63B 2220/833; A63B 24/0062; A63B 71/06; G01S 19/19; G04F 10/00; G04G 21/02; G07C 1/22; G06Q 10/0639; A61B 5/11; A61B 5/7275; A61B 5/681; A61B 2503/10; A61B 5/1112
See application file for complete search history.

(56) References Cited

U.S. PATENT DOCUMENTS 6,876,947 B1* 4/2005 Darley et al. ................. 702/160
7,927,253 B2  4/2011 Vincent et al.
(Continued)

FOREIGN PATENT DOCUMENTS

CN  102339358 A  2/2012
JP  2000033184 A  2/2000
(Continued)

OTHER PUBLICATIONS

Timex Run Trainer 1.0 GPS In-Depth Review. dcrainmaker.com. Online. Nov. 1, 2011. Accessed via the Internet. Accessed Jun. 22, 2015. <URL: http://www.dcrainmaker.com/2011/11/timex-run-trainer-gps-in-depth-review.html>.*

(Continued)

*Primary Examiner* — Dmitry Suhol
*Assistant Examiner* — Carl V Larsen
(74) *Attorney, Agent, or Firm* — Holtz, Holtz & Volek PC

(57) ABSTRACT

An exercise supporting device including a detecting section which repeatedly detects motion data relative to the exercise motion status of a user during the exercise motion; an analyzing and judging section which obtains, based on the motion data, a first motion information value corresponding to the user's moving speed and a second motion information value corresponding to the user's footstep count per unit time or footstep width at each time the detecting section detects the motion data, and judges whether the first motion information value is out of a first numerical value range and whether the second motion information value is out of a second numerical value range; and an output section which, when at least one of the motion information values is judged as being out of the relevant numerical value range, performs an informing operation regarding this motion information value.

14 Claims, 14 Drawing Sheets

(51) Int. Cl.
*A61B 5/11* (2006.01)
*G06Q 10/06* (2012.01)
*A61B 5/00* (2006.01)

(56) References Cited

U.S. PATENT DOCUMENTS

| | | | |
|---|---|---|---|
| 8,033,959 B2 | 10/2011 | Oleson et al. | |
| 8,221,290 B2 | 7/2012 | Vincent et al. | |
| 8,241,184 B2 | 8/2012 | DiBenedetto et al. | |
| 2004/0105690 A1* | 6/2004 | Naito et al. | 399/27 |
| 2007/0288157 A1* | 12/2007 | Peterman | 701/207 |
| 2008/0096726 A1* | 4/2008 | Riley et al. | 482/8 |
| 2008/0214903 A1* | 9/2008 | Orbach | 600/301 |
| 2008/0269644 A1* | 10/2008 | Ray | 600/587 |
| 2009/0048070 A1 | 2/2009 | Vincent et al. | |
| 2009/0233770 A1 | 9/2009 | Vincent et al. | |
| 2010/0265073 A1* | 10/2010 | Harper | 340/573.1 |
| 2011/0003665 A1* | 1/2011 | Burton et al. | 482/9 |
| 2011/0040440 A1* | 2/2011 | de Oliveira et al. | 701/30 |
| 2011/0275940 A1* | 11/2011 | Nims et al. | 600/483 |
| 2012/0015779 A1 | 1/2012 | Powch et al. | |
| 2012/0215328 A1* | 8/2012 | Schmelzer | 700/91 |
| 2012/0258433 A1* | 10/2012 | Hope et al. | 434/247 |
| 2012/0274469 A1 | 11/2012 | Oleson et al. | |
| 2012/0277040 A1 | 11/2012 | Vincent et al. | |
| 2012/0291564 A1* | 11/2012 | Amos et al. | 73/862.045 |
| 2013/0041617 A1 | 2/2013 | Pease et al. | |
| 2015/0066171 A1* | 3/2015 | Brussog et al. | 700/91 |

FOREIGN PATENT DOCUMENTS

| | | |
|---|---|---|
| JP | 2007125368 A | 5/2007 |
| JP | 2009050699 A | 3/2009 |
| JP | 2010-264246 A | 11/2010 |
| WO | 2012109244 A1 | 8/2012 |

OTHER PUBLICATIONS

Timex Ironman Global Trainer GPS—User Manual. Online. 2010. Accessed via the Internet. Accessed Jun. 22, 2015. <URL: http://assets.timex.com/user_guides/W260_M229/W260_M229_NA_EN.pdf!_ga=1.213312084.198490561.1434999192>.*

Chinese Office Action (and English translation thereof) dated Jul. 1, 2015, issued in counterpart Chinese Application No. 201310384899.7.

Japanese Office Action (and English translation thereof) dated Jun. 30, 2015, issued in counterpart Japanese Application No. 2012-188410.

* cited by examiner

FIG. 1A
FIG. 1B
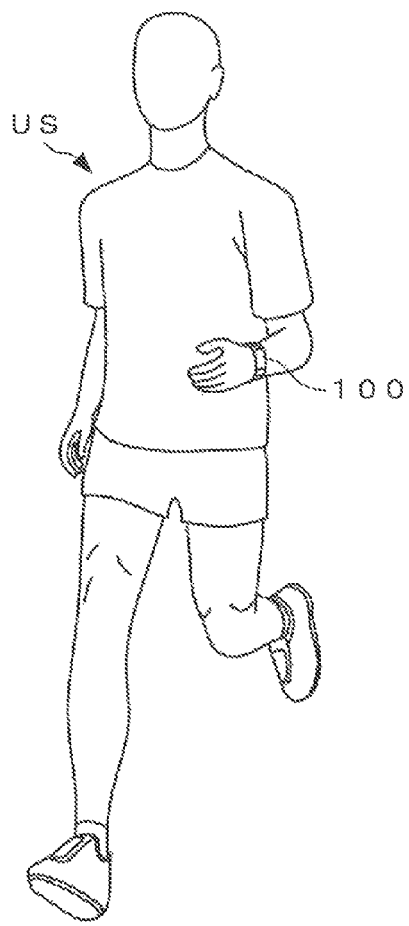
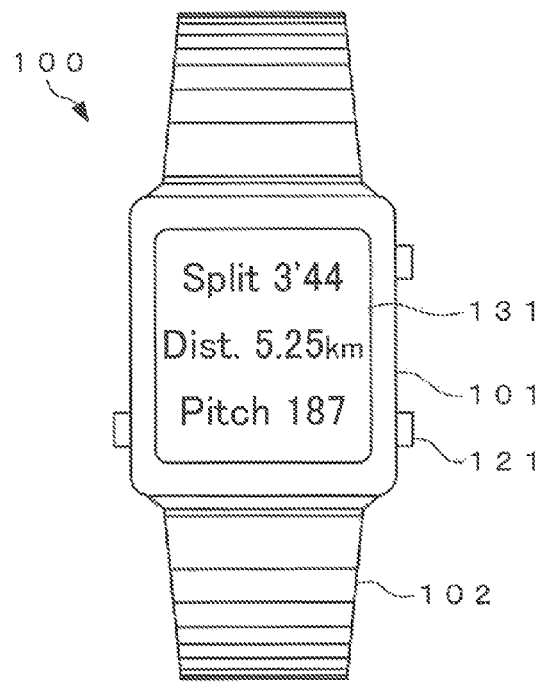

FIG. 5A

PACE DATABASE

| MOVEMENT DISTANCE RANGE (km) | LOWER-LIMIT TIME | STANDARD TIME | UPPER-LIMIT TIME |
|---|---|---|---|
| 0 ~ 5 | 3 MINUTES AND 55 SECONDS | 3 MINUTES AND 45 SECONDS | 3 MINUTES AND 35 SECONDS |
| 5 ~ 10 | 3 MINUTES AND 55 SECONDS | 3 MINUTES AND 45 SECONDS | 3 MINUTES AND 35 SECONDS |
| 40 ~ 42.195 | 4 MINUTES AND 0 SECONDS | 4 MINUTES AND 10 SECONDS | 4 MINUTES AND 20 SECONDS |

FIG. 5B

PITCH DATABASE

| MOVEMENT DISTANCE RANGE (km) | LOWER-LIMIT TIME | STANDARD TIME | UPPER-LIMIT TIME |
|---|---|---|---|
| 0 ~ 5 | 185 | 190 | 195 |
| 5 ~ 10 | 185 | 190 | 195 |
| 40 ~ 42.195 | 175 | 180 | 185 |

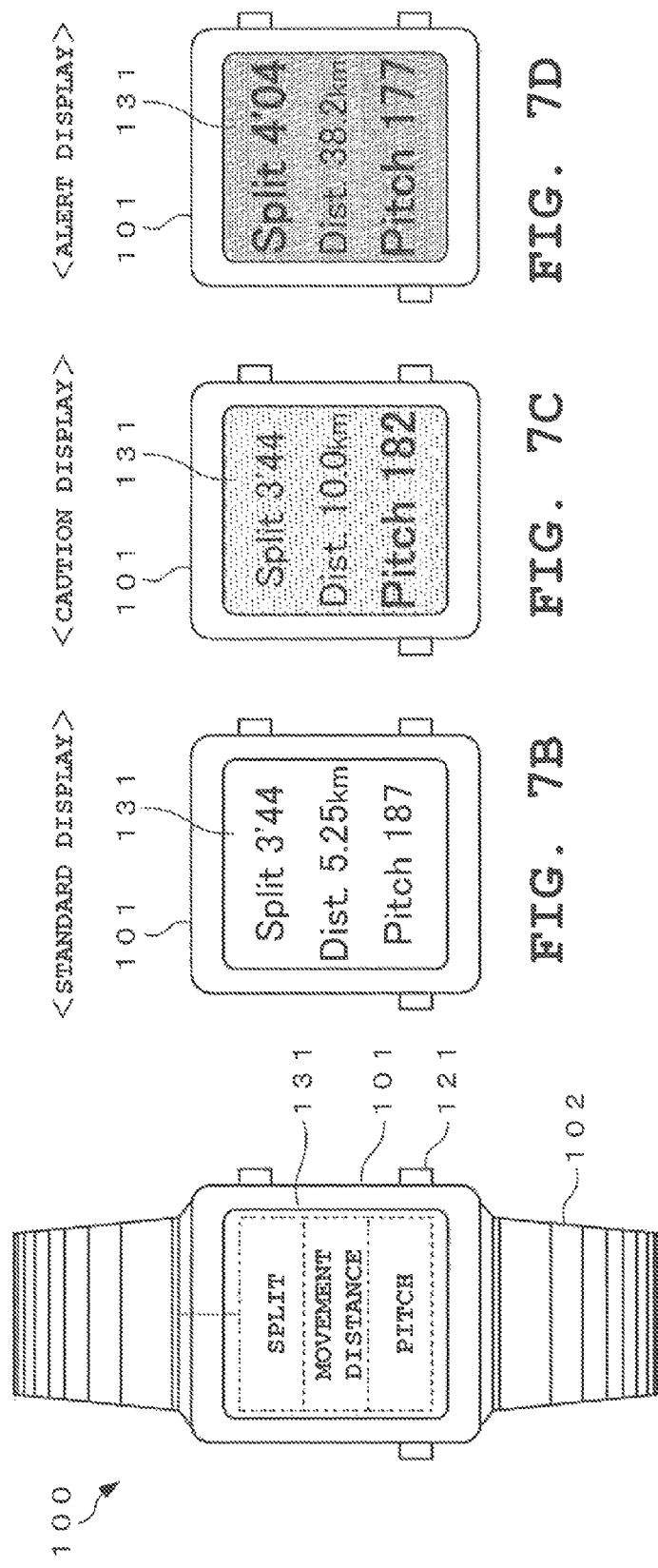

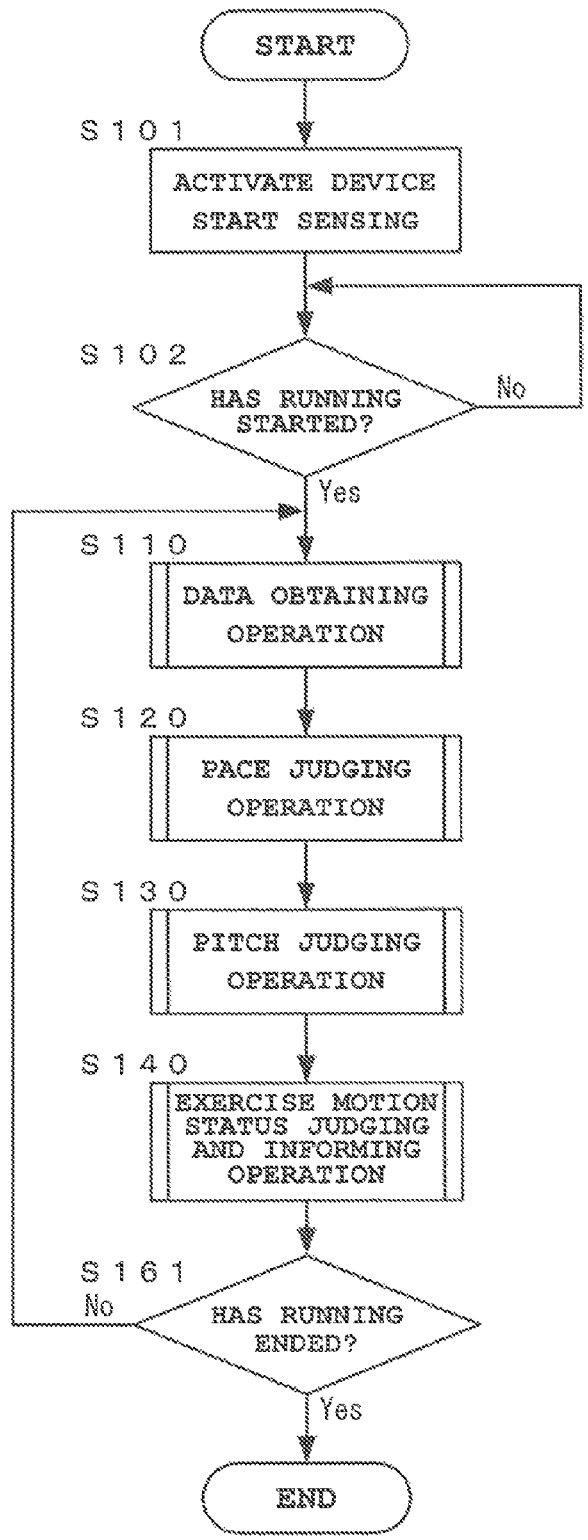

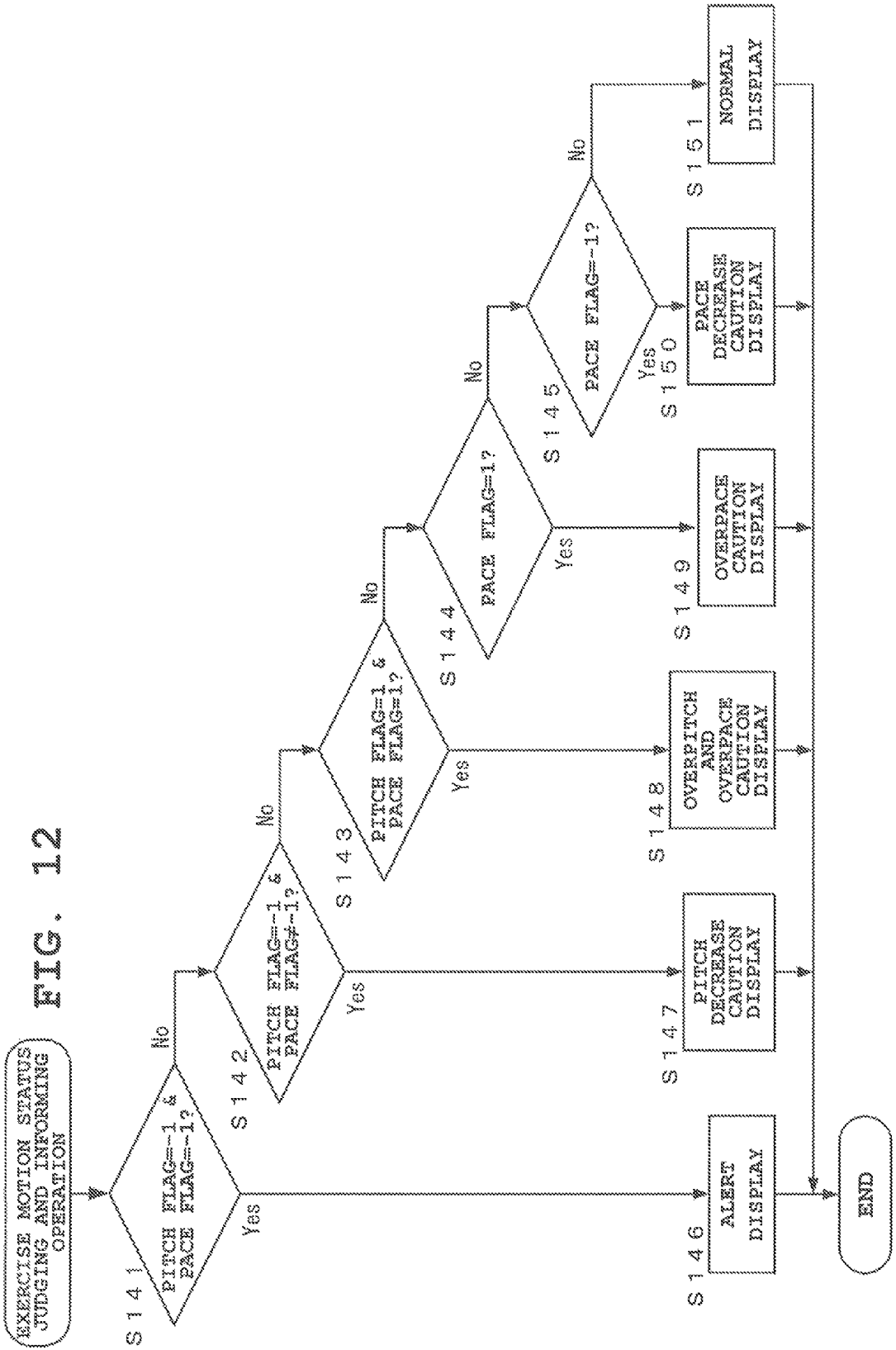

EXERCISE SUPPORTING DEVICE, EXERCISE SUPPORTING METHOD AND EXERCISE SUPPORTING PROGRAM

CROSS-REFERENCE TO RELATED APPLICATION

This application is based upon and claims the benefit of priority from the prior Japanese Patent Application No. 2012-188410, filed Aug. 29, 2012, the entire contents of which are incorporated herein by reference.

BACKGROUND OF THE INVENTION

1. Field of the Invention

The present invention relates to an exercise supporting device, an exercise supporting method and an exercise supporting program. Specifically, the present invention relates to an exercise supporting device, an exercise supporting method and an exercise supporting program applicable to ascertainment and improvement of the status of exercise motion by a user during a game, training, etc.

2. Description of the Related Art

In recent years, because of rising health consciousness, more and more people are performing daily exercises, such as running, walking and cycling, to maintain their wellness or improve their health condition. In addition, an increasing number of people are aiming to participate in a race such as a marathon race through these daily exercises. These people aiming to participate in a race have an objective of achieving a successful record in the race, and therefore are very conscious of and interested in efficient and effective training methods.

Currently, various devices to satisfy these demands are commercially available. For example, as a tool for runners, a running watch capable of measuring times such as a lap time and a split time has been known. Also, a running watch capable of measuring, in addition to times, a run distance and a speed (a pace) by using a GPS (Global Positioning System) has been known. In any of these devices, a measurement result until a point of time is displayed.

Regarding a device (system) including the function described above, an example is described in Japanese Patent Application Laid-Open (Kokai) Publication No. 2010-264246, in which various sensors such as a heart rate meter, an accelerometer, and a GPS receiver are worn by a user so as to detect various performance parameters such as a heart rate, a distance, a speed, a footstep count, and consumed calories and to provide these parameters to the user as information at a current point of time. Also, Japanese Patent Application Laid-Open (Kokai) Publication No. 2010-264246 describes a monitoring system for instructing the user to perform a predetermined training motion according to the detected performance parameters (the heart rate and the speed) at the current point of time based on a training routine set in advance.

During a marathon race or training such as running, even when running at the same pace as usual, the runner may be, for example, unconsciously extending a stride (a footstep width) to keep this running pace. In this case, overloading occurs in the stride, which may lead to excessive physical consumption and, as a result, accumulated fatigue that causes a decrease in pace in the latter half of the race or training.

Regarding this, in the above-described device or the method disclosed in Japanese Patent Application Laid-Open (Kokai) Publication No. 2010-264246, because the user (a runner) can only know the status of his or her own exercise motion from time information related to speeds at the time of running, such as a lap time, a split time, and a pace, a factor (a problematic point) causing a decrease in pace cannot be found, and a slowdown in the latter half of a race or training is difficult to be mitigated.

SUMMARY OF THE INVENTION

The present invention has an advantage of providing an exercise supporting device, an exercise supporting method and an exercise supporting program capable of specifically ascertaining the status of exercise motion by a user who is walking or running, recognizing the occurrence of a problem during the exercise motion, and improving the status of the exercise motion for the user to produce a better record.

In accordance with one aspect of the present invention, there is provided an exercise supporting device comprising: a detecting section which repeatedly detects motion data related to an exercise motion status of a user who is making an exercise motion by moving motion during the exercise motion of the user; an analyzing and judging section which obtains, based on the detected motion data, a first motion information value corresponding to a moving speed of the user and a second motion information value corresponding to a footstep count of the user per unit time or a footstep width of the user at each time the detecting section detects the motion data, judges whether the first motion information value is out of a first numerical value range at each time the first motion information value is obtained, and judges whether the second motion information value is out of a second numerical value range at each time the second motion information value is obtained wherein the first numerical value range is set as an allowable range of the first motion information value and the second numerical value range is set as an allowable range of the second motion information value; and an output section which, when at least one of the first motion information value and the second motion information value is judged by the analyzing and judging section as being out of a relevant one of the first numerical value range and the second numerical value range, performs an informing operation regarding the first motion information value or the second motion information value judged as being out of the relevant one of the first numerical value range and the second numerical value range, during the exercise motion of the user.

In accordance with another aspect of the present invention, there is provided an exercise supporting method comprising: a step of repeatedly detecting motion data related to an exercise motion status of a user who is making an exercise motion by moving motion during the exercise motion of the user; a step of obtaining, based on the detected motion data, a first motion information value corresponding to a moving speed of the user and a second motion information value corresponding to a footstep count of the user per unit time or a footstep width of the user at each time the motion data is detected; a step of judging whether the first motion information value is out of a first numerical value range which is set as an allowable range of the first motion information value, at each time the first motion information value is obtained; a step of judging whether the second motion information value is out of a second numerical value range which is set as an allowable range of the second motion information value, at each time the second motion information value is obtained; and a step of, when at least one of the first motion information value and the second motion information value is judged as being out of a relevant one of the first numerical value range and the second numerical value range, performing an informing operation regarding the first motion information value or the second motion information value judged as being out of the relevant one of the first numerical value range and the second numerical value range, during the exercise motion of the user.

In accordance with another aspect of the present invention, there is provided a non-transitory computer-readable storage medium having stored thereon an exercise supporting program that is executable by a computer, the program being executable by the computer to perform functions comprising: processing for repeatedly detecting motion data related to an exercise motion status of a user who is making an exercise motion by moving motion during the exercise motion of the user; processing for obtaining, based on the detected motion data, a first motion information value corresponding to a moving speed of the user and a second motion information value corresponding to a footstep count of the user per unit time or a footstep width of the user at each time the motion data is detected; processing for judging whether the first motion information value is out of a first numerical value range which is set as an allowable range of the first motion information value, at each time the first motion information value is obtained; processing for judging whether the second motion information value is out of a second numerical value range which is set as an allowable range of the second motion information value, at each time the second motion information value is obtained; and processing for, when at least one of the first motion information value and the second motion information value is judged as being out of a relevant one of the first numerical value range and the second numerical value range, performing an informing operation regarding the first motion information value or the second motion information value judged as being out of the relevant one of the first numerical value range and the second numerical value range, during the exercise motion of the user.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 1A and FIG. 1B are schematic structural views of an exercise supporting device according to a first embodiment of the present invention;

FIG. 5A and FIG. 5B are tables showing examples of a database for use in judging processing that is applied to the exercise supporting method according to the present invention;

FIG. 7A to FIG. 7D are diagrams showing examples of the informing operation that is applied to the exercise supporting method according to the present invention;

FIG. 8 is a flowchart showing an example of the exercise supporting method in an interface device according to the first embodiment;

FIG. 12 is a flowchart showing an example of an exercise motion status judging and informing operation in the exercise supporting method according to the first embodiment;

DETAILED DESCRIPTION OF THE PREFERRED EMBODIMENTS

Embodiments of the exercise supporting device, the exercise supporting method, and the exercise supporting program according to the present invention are described in detail below. In the following description, as examples of exercise motion by moving motion, cases are described where a user participates in a marathon race or conducts training such as running.

First Embodiment

Exercise Supporting Device

FIG. 1A and FIG. 1B are schematic structural views of an exercise supporting device of a first embodiment according to the present invention.

Figure 2:
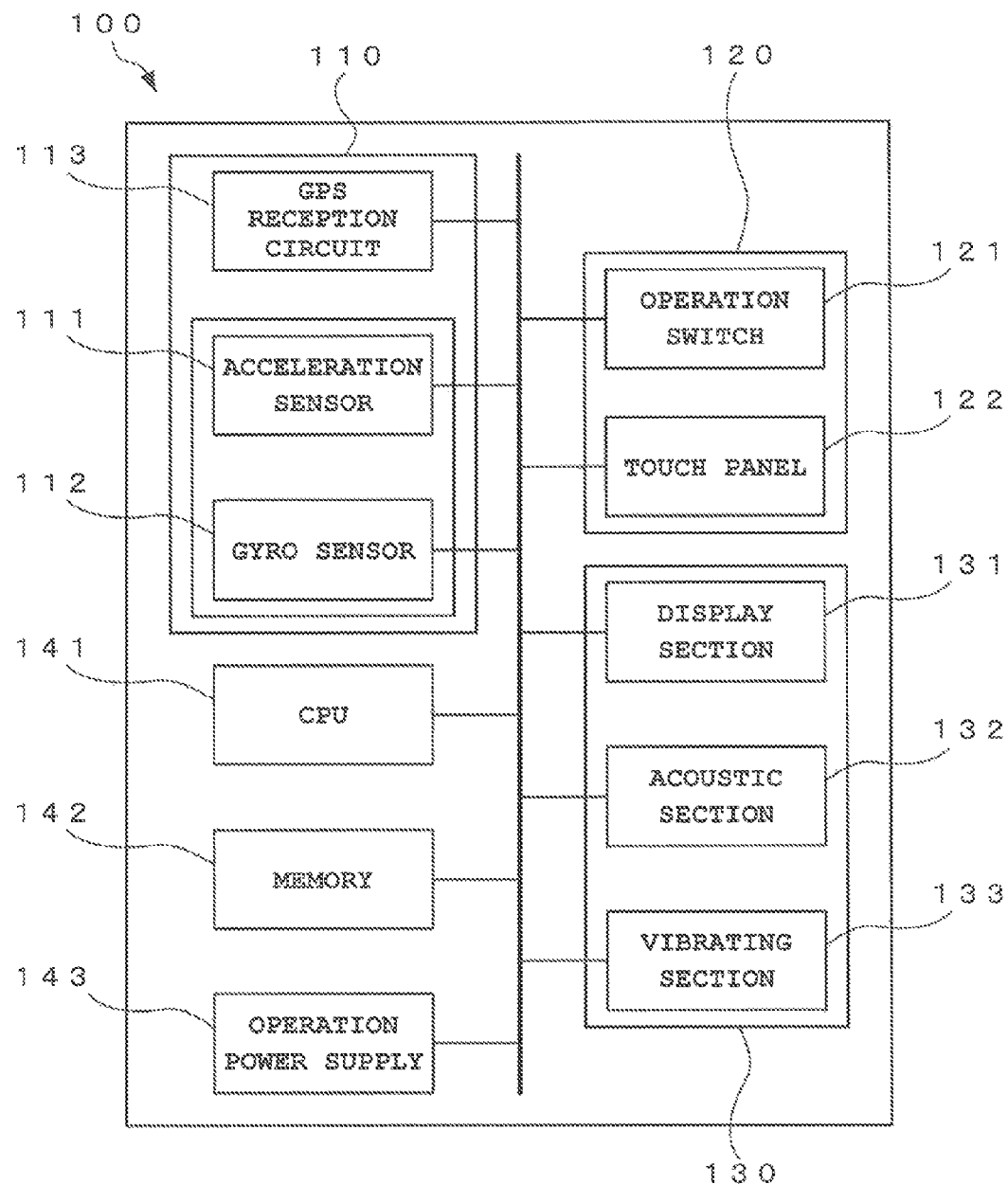
FIG. 2 is a block diagram showing an example of the structure of an interface device that is applied to the exercise supporting device according to the first embodiment.

FIG. 2 is a block diagram showing an example of the structure of an interface device that is applied to the exercise supporting device according to the first embodiment.

The exercise supporting device according to the present embodiment includes, for example, an interface device 100 that is worn around a wrist or the like of a user US, as depicted in FIG. 1A.

The interface device 100 has an outer appearance of, for example, a wrist watch as depicted in FIG. 1B, and includes a device body 101 having a display section 131 for providing predetermined information to the user and a belt section 102 that is wrapped around a wrist of the user US so that the device body 101 is worn around the wrist.

Specifically, the interface device 100 includes, for example, a sensor section (detecting section) 110, an input interface section (operating section) 120, an output interface section (output section) 130, a central computing circuit (hereinafter referred to as "CPU": analyzing and judging section) 141, a memory (storage section) 142, and an operation power supply 143, as depicted in FIG. 2.

The sensor section 110 has an acceleration sensor 111, a gyro sensor (angular velocity sensor) 112, and a GPS reception circuit (position sensor) 113, as depicted in FIG. 2.

The acceleration sensor 111 detects a change ratio of an operation speed (acceleration) when the user US is running.

The gyro sensor (angular velocity sensor) 112 detects a change in motion direction (angular velocity) when the user US is exercising.

By the CPU 141 executing a predetermined control program, a pace at the time of running (speed: first motion information value) and a pitch at the time of running (footstep count per unit time (for example, one minute): second motion information value) are measured or calculated based on a change tendency and waveform peak frequency of acceleration data obtained from detection by the acceleration sensor 111 and angular velocity data obtained from detection by the gyro sensor 112. The pace and the pitch are repeatedly obtained at each predetermined time interval from the time when the user US starts running.

In addition, based on the calculated pace and the elapsed time from the start of the exercise motion, a movement distance is obtained. These pitch, pace, and movement distance are mutually associated with a running time at each predetermined time interval and stored in a predetermined storage area of the memory 142.

The GPS reception circuit 113 receives electric waves from a plurality of GPS satellites to detect (geographical) position data composed of latitudes and longitudes. Based on the position data detected by the GPS reception circuit 113, a movement distance is obtained by the CPU 141. The GPS reception circuit 113 obtains a moving speed of the user US by using the Doppler shift effect of the electric waves from the GPS satellites.

Here, the movement distance and the moving speed obtained based on the position data detected by the GPS reception circuit 113 and the movement distance and the pace obtained based on the sensor data detected by the acceleration sensor 111 and the gyro sensor 112 described above are used together or mutually supplemented with each other, whereby the accuracy of the movement distance and the pace of the user US to be obtained can be increased.

That is, the sensor section 110 is not necessarily required to include the GPS reception circuit 113 as long as the acceleration sensor 111 and the gyro sensor 112 are included. However, by the sensor section 110 further including the GPS reception circuit 113 as described above, the accuracy of the movement distance and the pace of the user US to be obtained can be increased.

The input interface section 120 includes an operation switch 121 and a touch panel 122, as depicted in FIG. 2.

The operation switch 121 has, for example, a button switch, and is used to perform operations (sensing operations) such as starting, ending, and pausing detection and measurement of various data in the sensor section 110 described above. Also, it is used to set items to be displayed on the display section 131, and to perform operations such as inputting and setting a range of numerical values for use in an exercise supporting method, which will be described further below.

The touch panel 122 is placed on or integrally formed with a front surface of the display section 131. By an area corresponding to information displayed on the display section 131 being touched, a function corresponding to that information is selectively executed. Functions to be achieved by the touch panel 122 may be the same as functions to be achieved by the operation switch 121 described above, or may be unique to operations by the touch panel 122.

The input interface section 120 may include both of the operation switch 121 and the touch panel 122. Alternatively, in the configuration where functions to be achieved by the operation switch 121 are the same as functions to be achieved by the touch panel 122, the input interface section 120 may include only one of the operation switch 121 and the touch panel 122.

The output interface section 130 has the display section 131, an acoustic section 132, and a vibrating section 133, as depicted in FIG. 2.

The display section 131 has a display device such as a liquid-crystal display panel or an organic EL display panel, and displays an image including, for example, character information, based on various information obtained from sensor data detected by the sensor section 110, at least during exercise motion by the user described above.

On the display section 131, for example, character information including numerical values such as a movement distance "Dist.", a pace (split time "Split"), a pitch "Pitch", and a running time (omitted in the drawing) is displayed, as depicted in FIG. 1B. These pieces of information may be simultaneously displayed on the display section 131, or one or more pieces of information may be sequentially displayed by, for example, the operation of the operation switch 121 and the touch panel 122 described above.

The display section 131 displays exercise support information (such as a caution or alert) by a predetermined display method according to the status of an exercise motion by the user US analyzed and judged based on the exercise supporting method described below, and thereby performs an informing operation of visually informing the user US of the exercise support information.

Here, as a method of displaying exercise support information on the display section 131, for example, the following display methods a to d can be applied singly or in combination.

a. A method in which a numerical value is highlighted by setting the size of a character corresponding to the numerical value larger than others, setting the thickness of the line configuring the character larger than others, or setting the color of the character such that the color is different from and relatively more conspicuous than others.

b. A method in which, in place of or together with a numerical value, character information indicative of a corresponding specific message is highlighted for display.

c. A method in which the display color of a background portion in an entire or partial area of the display section 131 is changed for display.

d. A method in which a numerical value, character information indicative of a specific message, or the background portion is displayed and blinks.

Specific examples of these display methods will be described further below.

The acoustic section 132 has an acoustic device such as a buzzer or a loudspeaker. The acoustic section 132 uses the acoustic device, and thereby performs an informing operation of acoustically informing the user US of exercise support information (such as a caution or alert) according to the status of exercise motion by the user US analyzed and judged based on the exercise supporting method described below, by sound information such as a predetermined tone, a sound pattern, or an audio message.

The vibrating section 133 has a vibrating device such as a vibrating motor or a vibrator. The vibrating section 133 uses the vibrating device, and thereby tactually informs the user US of exercise support information (such as a caution or alert) according to the status of exercise motion by the user US, by vibration information such as a predetermined vibration pattern or its intensity.

The output interface section 130 includes at least the display section 131. However, it may include one of the acoustic section 132 and the vibrating section 133, or both of them, in addition to the display section 131.

In the case where the output interface section 130 includes a plurality of informing means such as the acoustic section 132 and the vibrating section 133 in addition to the display section 131, for example, the user US is informed of exercise support information (such as a caution or alert) firstly by sound information or vibration information, and thereby is prompted to check numerical value information or character information displayed on the display section 131. As a result of this configuration, the user US can be informed of exercise support information more reliably.

The memory 142, which includes a non-volatile memory, stores sensor data such as acceleration data, angular velocity data, and position data, and stores numerical value information such as a pitch, a pace, a movement distance at the time of running measured or calculated based on this sensor data, in association with the running time.

Here, the running time is set at a plurality of times at each predetermined time interval. Also, the time interval is set in advance to be, for example, one second to ten seconds.

The time interval may be set by the user US operating the input interface section 120 and may be changeably by the user US. Alternatively, the time interval may be a fixed value set in advance in the interface device 100 based on, for example, a time interval for the GPS reception circuit 113 to detect position data.

In the non-volatile memory portion of the memory 142, various data and information are stored which are generated by and referred to in an exercise supporting method (details will be described further below) to be executed in the interface device 100 according to the present embodiment.

Here, the memory 142 may include an a read-only memory (ROM) having stored therein control programs (software) for achieving predetermined functions for the sensor section 110, the input interface section 120, the output interface section 130, and the memory 142.

The CPU 141 includes a timer function and, by performing processing according to these control programs, controls the operations of the sensor section 110, the input interface section 120, the output interface section 130, and the memory 142 to achieve predetermined functions.

These control programs may be incorporated in advance in the CPU 141.

The non-volatile memory portion configuring the memory 142 may have, for example, a removable storage medium such as a memory card, which may be structured to be removable from and attachable to the interface device 100.

The operation power supply 143 supplies drive electric power to each section inside the interface device 100. As the operation power supply 143, a primary battery such as a commercially-available coin-type battery or a button-type battery, a secondary battery such as a lithium-ion battery or a nickel metal hydride battery, a power supply based on energy harvesting technology for generating electric power by energy such as vibration, light, heat, or electromagnetic waves, etc., can be adopted.

(Exercise Supporting Method; Sensor Data Analyzing Method and its Informing Method)

Next, an exercise supporting method in the exercise supporting device according to the present embodiment is described.

First, a sensor data analyzing method and its informing method to be applied to the exercise supporting method according to the present invention are described. Here, for clarification of features of the present invention, description will be made by verifying differences from a generally commercially-available (well-known) running watch.

Figure 3:
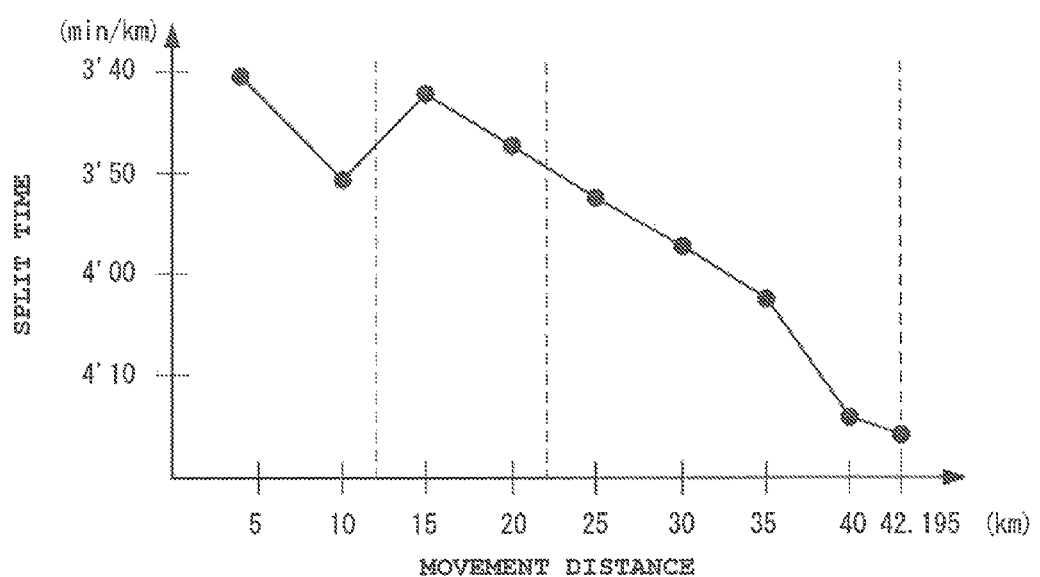
FIG. 3 is a graph showing an example of analyzing processing that is performed in a general running watch.

FIG. 3 is a graph showing an example of analyzing processing that is performed in a general running watch.

Depicted herein is an example of changes of a split time (time required for running 1 km and serving as a general running indicator indicative of a running speed) in a full marathon with 42.195 km for each movement distance of 5 km.

In a general running watch (comparative example), for example, a pace or a split time (on a vertical axis) with respect to movement distance (on a horizontal axis) is calculated as needed and thereby its change can be known, as depicted in a graph of FIG. 3.

That is, on the running watch, a pace or a split time during running is displayed as needed on the display section as numerical value information, and the user visually recognizes the numerical value information to ascertain his or her own exercise motion status.

Here, the graph depicted in FIG. 3 is specifically described. After a marathon starts, approximately from a point when the movement distance exceeds 15 km, the split time tends to gradually become longer (that is, the pace tends to gradually become slower).

On the other hand, until the movement distance is approximately 25 km, the split time comes approximately within a range of 3' 40 to 3' 50 min/km. Accordingly, the user recognizes that the pace can be kept approximately within a predetermined range until the movement distance is approximately 25 km. Thereafter, the pace of the user further decreases. However, as will be described further below, the user has not been able to ascertain that the running style until the movement distance is approximately 25 km is a factor in decreasing the pace.

That is, at the point when the movement distance exceeds 25 km, the user recognizes that the split time at the current point of time displayed on the running watch has become longer and the pace has become significantly decreased to be out of the range described above. In response, the user tries to improve the status.

However, as will be described further below, although the running style before the movement distance is 25 km is actually a factor in decreasing the pace, this cannot be ascertained when the conventional running watch is used. Accordingly, an inappropriate running style has been actually performed until the movement distance is 25 km, and it is difficult to improve the pace thereafter. This results in a slowdown in the latter half of the race as depicted in FIG. 3, and makes it difficult to improve the running status and produce a better record.

That is, as depicted in FIG. 3, when the pace or the split time changes, the running style before the point when the movement distance is 25 km is actually a factor in decreasing the pace thereafter. If this factor can be ascertained and improved, there is a possibility that a decrease in pace in the latter half of the race can be suppressed.

However, with the numerical value information displayed on the general running watch, this factor cannot be precisely ascertained.

Thus, the exercise supporting method according to the present invention has a feature of providing analysis results which allow a factor that causes a decrease in pace during exercise such as a race or training at a time ahead of the current time (in the future; for example, in the latter half of the race or training) to be precisely ascertained. This factor is provided via a display section of an interface device that can be visually and easily recognized by the user during exercise motion, whereby the user can recognize the occurrence of the factor that causes a decrease in pace at the time of the occurrence.

Figure 4:
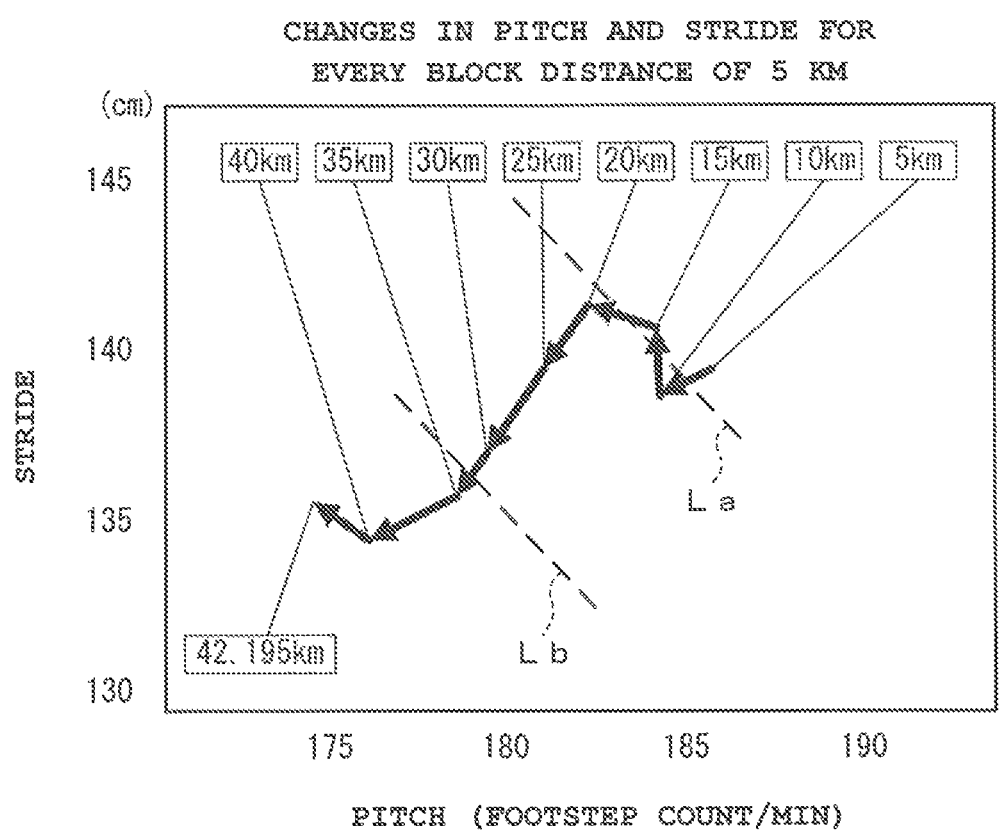
FIG. 4 is a graph showing an example of analyzing processing that is applied to an exercise supporting method according to the present invention.

FIG. 4 is a graph showing an example of analyzing processing that is applied to an exercise supporting method according to the present invention.

FIG. 5A and FIG. 5B are tables showing examples of a database for use in judging processing that is applied to the exercise supporting method according to the present invention.

In the exercise supporting method according to the present invention, the CPU 141 performs the following analyzing processing.

First, during exercise (running) of the user US, the CPU 141 splits the pace (speed) calculated based on the sensor data detected by the sensor section 110 into a component of a pitch (a footstep count) and a component of a stride (a footstep width). Here, a relation of "pace-pitch×stride" is held. Therefore, for example, a stride can be automatically calculated if a pace and a pitch are revealed based on the sensor data detected by the sensor section 110.

The relation between pitch and stride is plotted as a graph by setting pitches on the horizontal axis and strides on the vertical axis, as depicted in FIG. 4. In this graph, when the pace is constant, the pace is represented as straight lines La and Lb going downward to the right in the drawing, as indicated by dashed lines in the drawing.

In FIG. 4, the straight line La is a pace reference line indicating a relation between pitch and stride when a section distance of 5 km is moved at a pace of nineteen minutes. The straight line Lb is a pace reference line indicating a relation between pitch and stride when the section distance of 5 km is moved at a pace of twenty minutes. Bold arrows sequentially represent changes in pitch and stride for each section distance of 5 km in a full marathon of 42.195 km correspondingly to the movement distance.

For each of items including the pace, the pitch, and the stride measured or calculated during exercise motion of the user, by referring to a database with a numerical value range set in advance as an allowable range as depicted in FIG. 5A and FIG. 5B, the CPU 141 judges whether the relevant item is out of the numerical value range in a movement distance range. Here, the numerical value range to be applied to judging processing is set for each of a plurality of movement distance ranges for each predetermined distance (for example, a section distance of 5 km), as depicted in FIG. 5A and FIG. 5B. The numerical value range set for each movement distance range has an upper-limit value, a lower limit value, and a standard value at the midpoint between the upper-limit value and the lower-limit value. Here, a range from the lower-limit value to the upper-limit value including the lower-limit value and the upper-limit value is an allowable range.

FIG. 5A depicts a database with a numerical value range about paces being set, and FIG. 5B depicts a database in which a numerical value range about pitches has been set. As described above, since a stride can be calculated based on a pace and a pitch, a numerical value range about strides is also set by setting the numerical value ranges of paces and pitches.

The upper-limit value, the lower-limit value, and the standard value in each of these numerical value ranges may be set by, for example, the user inputting a value (in advance) prior to the start of exercise motion by using the operation switch 121 or the touch panel 122 of the input interface section 120. Alternatively, typical numerical values may be set in advance based on age, gender, previous race records, etc.

The numerical value ranges with pace, pitch and stride being set are stored as a pace database, a pitch database, and a stride database in a predetermined storage region of the memory 142.

The results in the analyzing processing and the judging processing described above can be visibly recognized by using the graph depicted in FIG. 4.

That is, it can be judged in the graph depicted in FIG. 4 that a relation between pitch and stride of the user US in a full marathon of 42.195 km is changed at a point when the movement distance is approximately 20 km to 25 km from the start so as to be directed in a direction downward to the left from the straight line La, which means that the pace rapidly goes down.

In addition, in FIG. 4, not only the change in pace at the point of approximately 20 km to 25 km described above but also, prior to the change, a decrease in pitch occurs from a point when the movement distance is approximately 10 km, and therefore the pitch cannot be kept in a predetermined state. It can be judged that the running style has been such that the stride is increased against the above-described state to keep the pace approximately constant. Also, it can be estimated that this running style causes a slowdown in the latter half of the race. That is, it can be analyzed that a factor causing the slowdown in the latter half of the race has already occurred from the point when the movement distance is approximately 10 km.

Then, the user US is informed of the analysis results obtained through the series of processing described above, by the informing method described below, and thereby can precisely ascertain (specify) a factor that causes a slowdown in the latter half of the race (problematic point), improve the running style, and produce a better record.

Figure 6A:
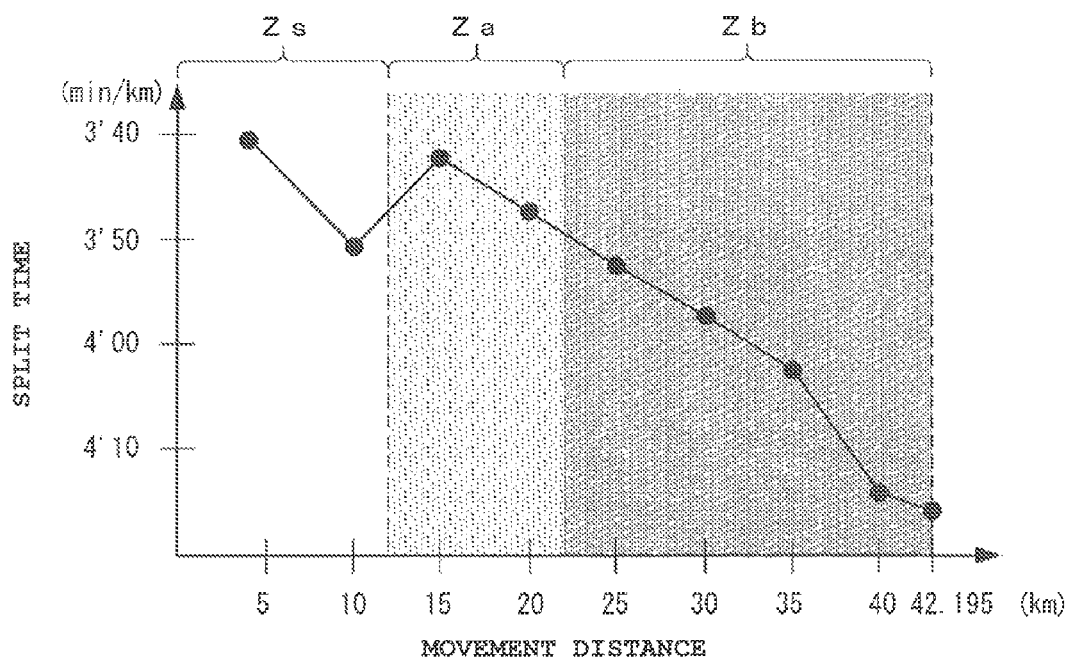
FIG. 6A and FIG. 6B are diagrams showing examples of analysis results for use in informing operation that is applied to the exercise supporting method according to the present invention.
Figure 6B:
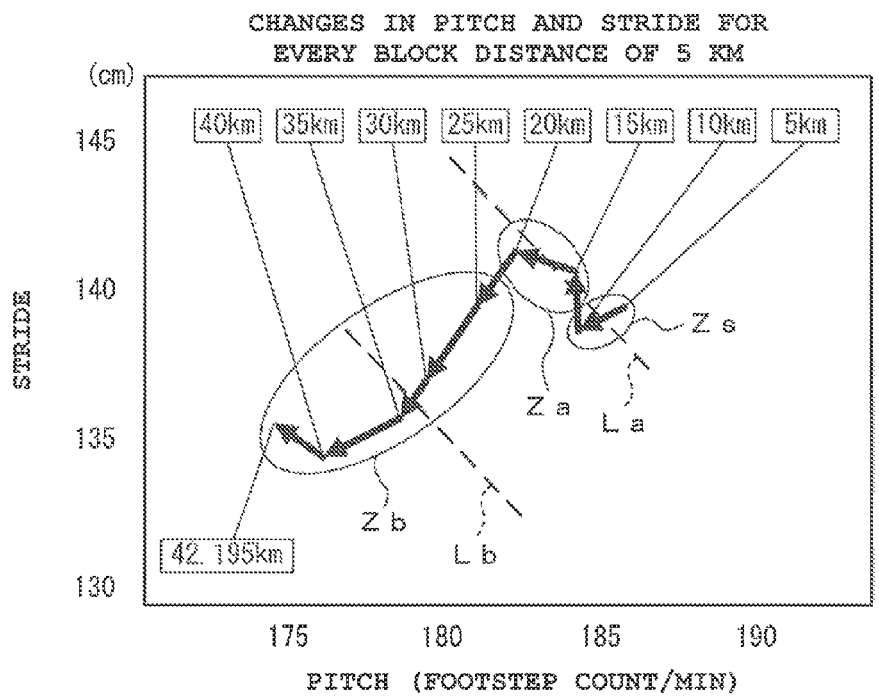

FIG. 6A and FIG. 6B are diagrams showing examples of analysis results for use in informing operation that is applied to the exercise supporting method according to the present invention.

FIG. 7A to FIG. 7D are diagrams showing examples of the informing operation that is applied to the exercise supporting method according to the present invention. Here, these drawings depict examples of a display operation, which is a feature of the informing method according to the present invention.

In FIG. 6A, FIG. 7C and FIG. 7D, a caution display area and an alert display area, and a caution display state and an alert display state are depicted by being hatched for convenience of explanation.

First, on the display section 131 of the interface device 100, character information including numerical values of the split time "Split", the movement distance "Dist.", and the pitch "Pitch" are displayed on upper, middle and lower levels, respectively, as display items of the exercise support information, as depicted in FIG. 7A and FIG. 7B.

Here, each numerical value at the current point of time obtained based on sensor data detected by the sensor section 110 described above is displayed on the display section 131.

Note that the display items on the display section 131 are not limited to these, and other information such as other numerical values and specific character information may be displayed. Alternatively, one or plurality of pieces of information may be displayed in any display format.

Then, the CPU 141 performs the above-described analyzing method and thereby judges, based on each of the pace, the pitch, and the stride obtained based on the sensor data detected by the sensor section 110 during exercise (running) of the user US, whether each item is within or out of the numerical value range (allowable range) set in advance in the database.

Then, when judged that one of the pace, the pitch, and the stride has exceeded the set numerical value range, the CPU 141 judges that this item has a problem, and thereby causes character information including the numerical value of this item to be displayed on the display section 131 and performs caution display or alert display to prompt the user US to improve the running style.

Here, specific examples of the caution display and the alert display on the display section 131 are as follows. As depicted in FIG. 7C, highlighting is performed in any of the following manners: (1) the size of a character corresponding to the numerical value of the item out of the set numerical value range is increased from the size at normal time (in a standard display state, which will be described further below), (2) the thickness of lines constituting the character is increased from that at normal time, and (3) the color of the character is set to be different from and relatively more conspicuous than the color at normal time. Alternatively, as depicted in FIG. 7D, display is made in any of the following manners: (4) the display color of the background portion in an entire or partial area of the display section 131 is set as, for example, a caution color such as yellow or an alert color such as red, (5) in place of or together with a numerical value, a corresponding specific message is highlighted, and (6) a numerical value, character information indicative of a specific message, or the background portion is displayed and blinks. Still alternatively, the plurality of these display methods are combined and applied.

Next, a specific example of the informing operation when, for example, the running style of the user US is in a state depicted in the graphs of FIG. 3 and FIG. 4 described above is described.

In the case of the running style depicted in FIG. 3 and FIG. 4, as described above, the pace (split time), the pitch, and the stride are all kept in the respective numerical value ranges (allowable ranges) set in advance in the databases, from the start until the movement distance is approximately 10 km.

Here, the CPU 141 judges that the running style of the user US is in a favorable or normal state. The judgment result (that is, the analysis result in the analyzing method described above) is represented as a standard display area "Zs" for convenience of explanation in FIG. 6A and FIG. 6B.

Based on this judgment result, the CPU 141 causes each item to be displayed in a standard display state on the display section 131 of the interface device 100, as depicted in FIG. 7B. In the standard display state, for example, neither highlighting of each item of the numerical value information nor an operation of letting the background portion of the display section 131 glow in a specific color is performed, as depicted in FIG. 7B.

Next, when the movement distance is over 10 km, the pace is kept approximately constant, but the stride tends to increase to compensate for a decrease in pitch, and therefore the stride is out of the numerical value range set in advance. Here, the CPU 141 judges that the pitch has a problem. The judgment result (analysis result) is represented as a caution display area "Za" for convenience in FIG. 6A and FIG. 6B.

Based on the judgment result, the CPU 141 causes the character indicating the numerical value of the pitch "Pitch" on the display section 131 to be highlighted, as depicted in FIG. 7C. The CPU 141 also causes the background portion of the display section 131 to be displayed in a caution display state with the display color being set as a caution color such as yellow. As a result, the user US is informed that the pitch has a problem and is prompted to improve the running style.

Then, the user US views this caution display, ascertains his or her own running style, and runs while consciously correcting the pitch, whereby a possibility of suppressing excessive physical exhaustion to avoid a slowdown in the latter half of the race is increased.

Note that, although the example has been described in which caution display, such as that depicted in FIG. 7C, is performed when the pitch is decreased while the pace is being kept approximately constant, the present invention is not limited thereto.

That is, the caution display may be performed when the pace is out of the preset numerical value range while the pitch is being kept, or when one of the pace, the pitch, and the stride exceeds the preset numerical value range.

On the other hand, when the above-described caution display is performed but the user US cannot correct the pitch, both of the pace (split time) and the pitch tend to significantly decrease and the stride tends to be narrowed, for example, as depicted for the movement distance exceeding 20 km in the drawings. That is, all the items exceed the numerical value range set in advance. Accordingly, the CPU 141 judges that both of the pace and the pitch have a problem. Here, the judgment result (analysis result) is represented as an alert display area "Zb" for convenience of explanation in FIG. 6A and FIG. 6B.

Based on the judgment result, the CPU 141 causes the characters indicating numerical values of the split time "Split" and the pitch "Pitch" of the display section 131 to be highlighted and causes the background portion of the display section 131 to be displayed in an alert display state where the display color of the background portion of the display section 131 is an alert color such as red. As a result, the user US is informed that both of the pace and the pitch have a problem and is prompted to improve the running style.

In the informing operation described above, the informing method has been described in which caution display or alert display is performed when one of the pace, the pitch, and the stride obtained based on the sensor data is out of the set numerical value range.

However, the present invention is not limited thereto. For example, between the case where one of the pace, the pitch, and the stride is above the set numerical value range (exceeds and is out of the upper-limit value) and the case where one of the pace, the pitch, and the stride is below the set numerical value range (does not satisfy and is out of the lower-limit value), the color of the character indicating the numerical value of the corresponding item may be set differently to perform caution display or alert display.

Also, in the above-described informing operation, a different display color may be used and displayed for each of the display items such as the pace, the pitch, and the stride so that the user US can intuitively ascertain the exercise motion status (running status) at the current point of time and can easily recognize the problematic point even if the user US during exercise (running) views the display section 131 of the interface device 100 for an extremely brief moment.

Moreover, in addition to the informing operation of visually displaying the exercise support information via the display section 131 described above, a sound may be emitted from the acoustic section 132 of the output interface section 130 or vibrations may be generated from the vibrating section 133 of the output interface section 130 to notify the user US of a change in the exercise motion status or the occurrence of a problematic point.

Furthermore, an informing operation according to the level of skill of the user US may be performed. That is, if the user US is an expert at marathons and running, as described above, a specific numerical value may be displayed on the display section 131 of the interface device 100 to perform the informing operation such as caution display and alert display, whereby the user US can relatively easily ascertain his or her own exercise motion status, recognize a problematic point, and effectively utilize the result to improve the running style and produce a better record.

If the user is a beginner in marathons and running, when a specific numerical value is displayed on the display section 131 of the interface device 100 to perform the informing operation such as caution display and alert display, there is a possibility that the user cannot sufficiently ascertain and recognize his or her own exercise motion status and a problematic point or may take long time to do so and therefore the result cannot be sufficiently utilized to improve the running style and produce a better record.

Accordingly, in place of specific numerical value information on the display section 131 as described above or together with the numerical value information, for example, character information including a message (text) which specifically instructs the user how to improve the item having a problem, such as "increase the pitch" or "extend the stride", may be displayed.

Furthermore, in this case, a configuration may be adopted in which the user is reliably informed of the exercise support information by also using the informing method of emitting a sound or generating vibrations, as described above.

This switching among the informing operations is inputted and set by using, for example, the operation switch 121 and the touch panel 122 of the input interface section 120.

(Exercise Supporting Method; Entire Operation)

Next, the entire operation of an exercise supporting method to which the analyzing method and the informing method described above have been applied is described. Here, when necessary, description is made with reference to FIG. 3 to FIG. 7A to FIG. 7C used in the description of the analyzing method and the informing method described above.

FIG. 8 is a flowchart showing an example of the exercise supporting method in an interface device according to the first embodiment.

In the exercise supporting method in the interface device 100 according to the present embodiment, as depicted in FIG. 8, the CPU 141 first activates the interface device 100 to start a sensing operation of the acceleration sensor 111, the gyro sensor 112, and the GPS reception circuit 113 of the sensor section 110 (Step S101).

Specifically, as depicted in FIG. 1 and FIG. 2, the user US operates the operation switch 121 and the touch panel 122 of the input interface section 120 of the mounted interface device 100 to activate the interface device 100, and the CPU 141 controls the sensor section 110 to start an operation of detecting acceleration data, angular velocity data, and GPS data (position data or moving speed) by the acceleration sensor 111, the gyro sensor 112, and the GPS reception circuit 113 or enters a standby state where it can start these detections.

Next, the CPU 141 waits for the user US to start running (No at Step S102). When it is detected that the user US has started running (Yes at Step S102), the CPU 141 performs a data obtaining operation of obtaining data related to the exercise motion status of the user US (Step S110).

Here, the CPU 141 may detect that the user US has started running based on the detection of the movement of the position of the user US by the sensor section 110 or by detecting that the user US has pressed, for example, a start button switch provided to the operation switch 121 or a start button provided on the touch panel 122.

Next, the CPU 141 performs a pace judging operation (Step S120), a pitch judging operation (Step S130), and an exercise motion status judging and informing operation (Step S140).

Hereafter, the CPU 141 repeats the data obtaining operation, the pace judging operation, the pitch judging operation, and the exercise motion status judging and informing operation until the end of running (Step S110 to S140 and No at Step S161).

This repetition is performed at each running time set at a plurality of times for each preset constant time interval.

Then, when the end of running is detected (Yes at Step S161), the operation ends. The end of running is detected by detecting that, for example, the user US has pressed a stop button switch provided on the operation switch 121 or a stop button provided on the touch panel.

Next, each operation of the exercise supporting method is described.

Figure 9:
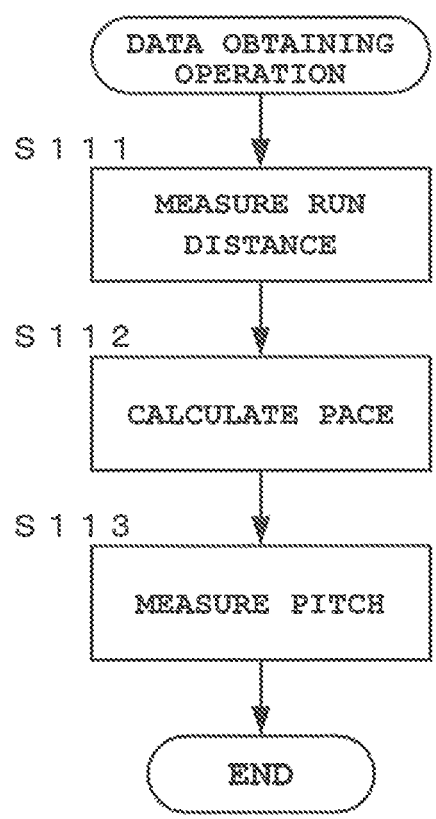
FIG. 9 is a flowchart showing an example of a data obtaining operation in the exercise supporting method according to the first embodiment.

FIG. 9 is a flowchart showing an example of a data obtaining operation in the exercise supporting method according to the first embodiment.

Figure 10:
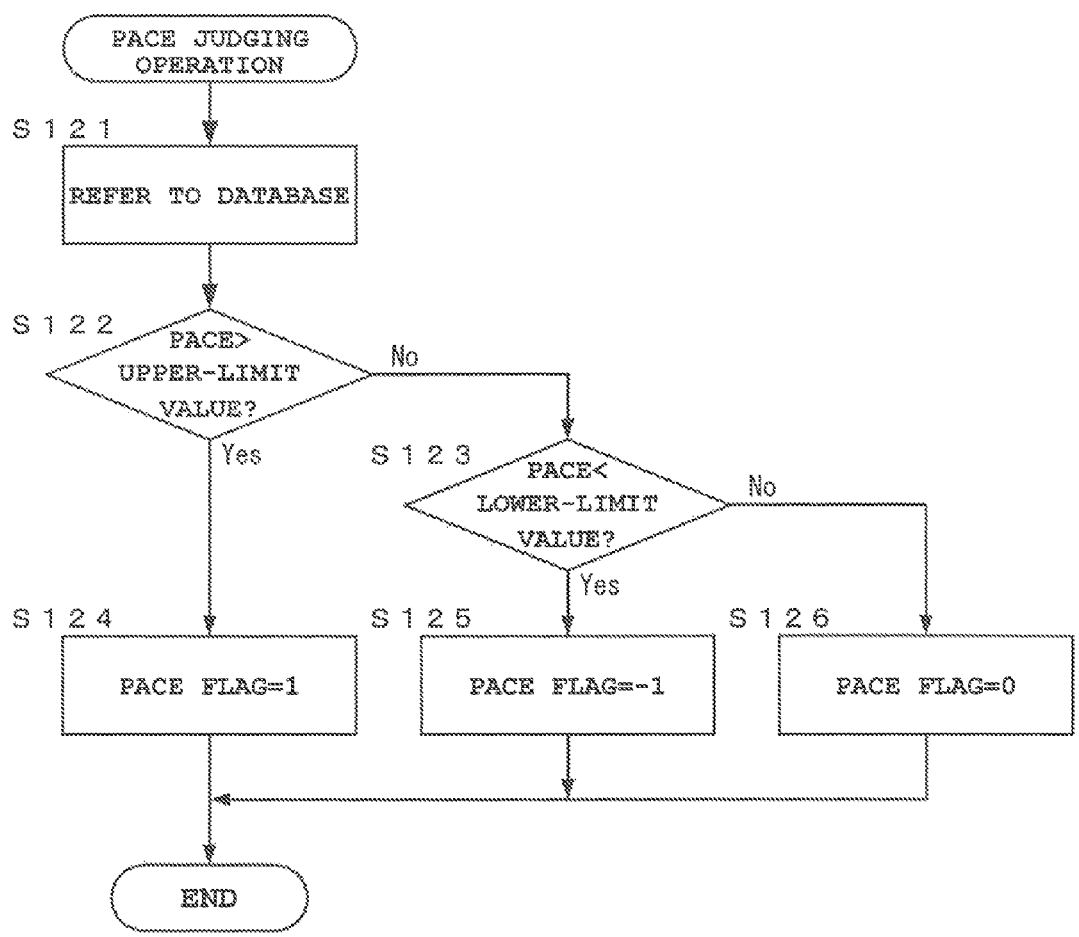
FIG. 10 is a flowchart showing an example of a pace judging operation in the exercise supporting method according to the first embodiment.

FIG. 10 is a flowchart showing an example of a pace judging operation in the exercise supporting method according to the first embodiment.

Figure 11:
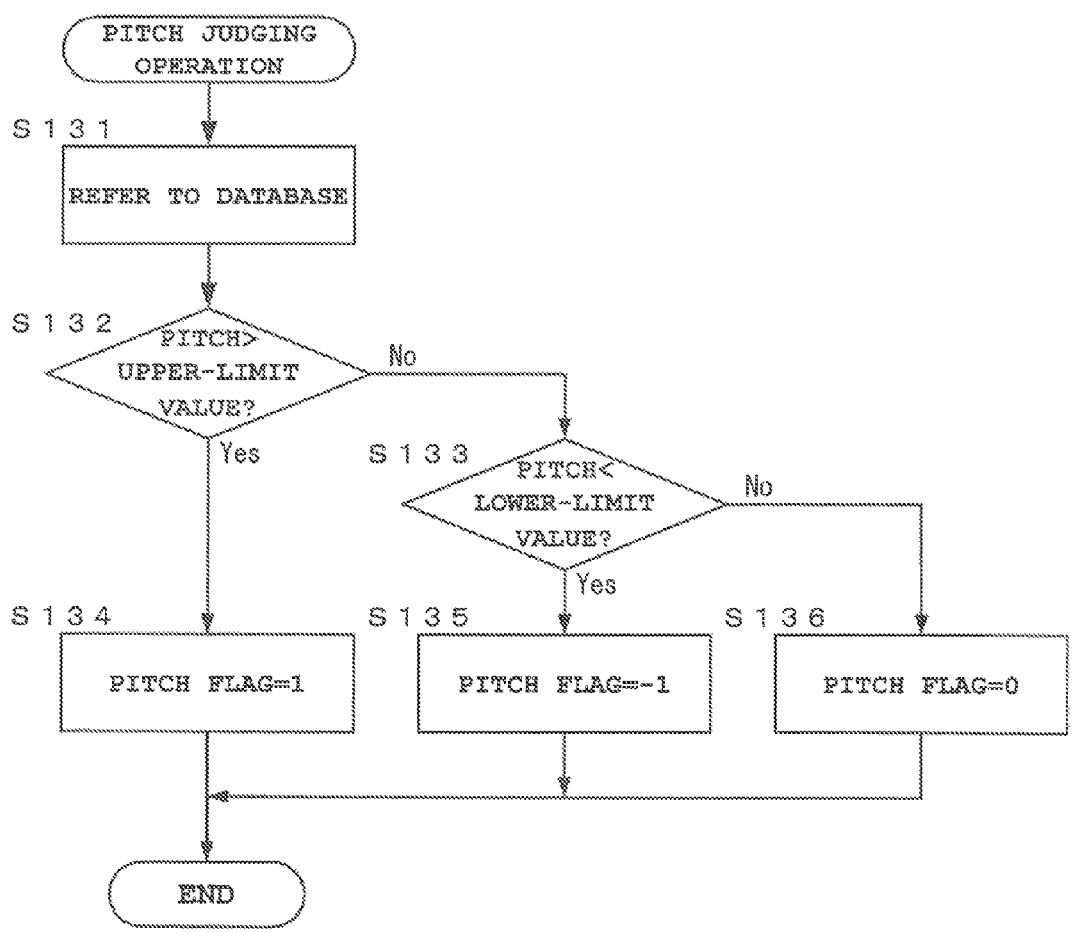
FIG. 11 is a flowchart showing an example of a pitch judging operation in the exercise supporting method according to the first embodiment.

FIG. 11 is a flowchart showing an example of a pitch judging operation in the exercise supporting method according to the first embodiment.

FIG. 12 is a flowchart showing an example of an exercise motion status judging and informing operation in the exercise supporting method according to the first embodiment.

(Data Obtaining Operation S110)

In the data obtaining operation S110, as depicted in the flowchart of FIG. 9, the CPU 141 stores the acceleration data, the angular velocity data, and the GPS data detected by the respective sensors described above in predetermined areas of the memory 142 in association with the running time. Here, the running time is an elapsed time from the start of running.

Next, the CPU 141 obtains a movement distance, a pace, and a pitch at the current point of time by measurement and calculation based on the acceleration data, the angular velocity data, and the GPS data detected by the respective sensors described above (Step S111 to S113).

Specifically, a pitch and a pace are obtained by measurement and calculation based on a change tendency and waveform peak frequency of the acceleration data and the angular velocity data.

Then, based on the obtained pace and running time (elapsed time), a movement distance is further obtained. The GPS data is used to enhance accuracy of the movement distance and the pace described above. These movement distance, pace, and pitch are stored in a predetermined storage region of the memory 142 in association with the running time.

(Pace Judging Operation S120)

In the pace judging operation S120, as depicted in the flowchart of FIG. 10, the CPU 141 refers to the pace database in which the numerical value range has been set in advance as depicted in FIG. 5A (Step S121) to compare the pace calculated in the above-described data obtaining operation S110 and the numerical value range set in the database, and thereby judges whether a problematic point about the pace has occurred.

Specifically, the CPU 141 first refers to the pace database stored in the memory 142 to extract the upper-limit value and the lower-limit value of the numerical value range set for a movement distance range including a current movement distance.

Next, the CPU 141 judges whether the above-described calculated pace is larger than the upper-limit value of the numerical value range (Step S122).

When the pace is larger than the upper-limit value of the set numerical value range, the CPU 141 sets a pace flag at "1" (Step S124), and stores the pace flag in a predetermined storage region of the memory 142.

On the other hand, when the pace is equal to or smaller than the upper-limit value of the set numerical value range, the CPU 141 further judges whether the pace is smaller than the lower-limit value of the set numerical value range (Step S123).

When the pace is smaller than the lower-limit value of the set numerical value range, the CPU 141 sets the pace flag at "−1" (Step S125), and stores the pace flag in the predetermined storage region of the memory 142.

That is, when the pace at the current point of time is out of the numerical value range set in advance, the pace flag is set up according to the out-of-range status (exceeding the upper-limit value or not satisfying the lower-limit value).

On the other hand, when the pace is equal to or larger than the lower-limit value of the set numerical value range, the CPU 141 judges that the pace is within the set numerical value range, sets the pace flag at "0" (Step S126), and then stores the pace flag in the predetermined storage region of the memory 142. Here, the pace flag is stored in the memory 142 in association with the running time.

(Pitch Judging Operation S130)

In the pitch judging operation S130, as depicted in the flowchart of FIG. 11, the CPU 141 refers to the pitch data base in which the numerical value range has been set in advance as depicted in FIG. 5B (Step S131) to compare the pitch measured in the above-described data obtaining operation S110 and the numerical value range set in the database, and thereby judges whether a problematic point about the pitch has occurred.

Specifically, the CPU 141 first refers to the pitch database stored in the memory 142 to extract the upper-limit value and the lower-limit value of the numerical value range set for a movement distance range including a current movement distance.

Next, the CPU 141 judges whether the above-described measured pitch is larger than the upper-limit value of the numerical value range (Step S132).

When the pitch is larger than the upper-limit value of the set numerical value range, the CPU 141 sets a pitch flag at "1" (Step S134), and stores the pitch flag in a predetermined storage region of the memory 142.

On the other hand, when the pitch is equal to or smaller than the upper-limit value of the set numerical value range, the CPU 141 further judges whether the pitch is smaller than the lower-limit value of the set numerical value range (Step S133).

When the pitch is smaller than the lower-limit value of the set numerical value range, the CPU 141 sets the pitch flag at "−1" (Step S135), and stores the pitch flag in the predetermined storage region of the memory 142.

That is, when the pitch at the current point of time is out of the numerical value range set in advance, the pitch flag is set up according to the out-of-range status (exceeding the upper-limit value or not satisfying the lower-limit value).

On the other hand, when the pitch is equal to or larger than the lower-limit value of the set numerical value range, the CPU 141 judges that the pitch is within the set numerical value range, sets the pitch flag at "0" (Step S136), and then stores the pitch flag in the predetermined storage region of the memory 142. Here, the pitch flag is stored in the memory 142 in association with the running time.

(Exercise Motion Status Judging Operation and Informing Operation S140)

In the exercise motion status judging operation and informing operation S140, based on the pace flag and the pitch flag set in the pace judging operation S120 and the pitch judging operation S130 described above, an exercise motion status and its problematic point of the user US are judged and, according to the judged exercise motion status and its problematic point, the user US is informed of exercise support information via the interface device 100, as depicted in the flowchart of FIG. 12.

Specifically, the CPU 141 first reads the pace flag and the pitch flag stored in the memory 142 based on the running time.

Next, the CPU 141 judges whether the condition is satisfied where the read pitch flag indicates "−1" and the read pace flag indicates "−1" (Step S141).

When the pitch flag and the pace flag satisfy the condition of the judging processing (Step S141), the CPU 141 judges that both of the pitch and the pace of the user US at the current point of time are each below the set numerical value range (each do not satisfy the lower-limit value) and being decreased, and causes the output interface section 130 to perform a predetermined alerting operation (Step S146).

Regarding the alerting operation performed herein, as described as the alert display state in the analyzing method and the informing method described above, for example, the following methods can be applied singly or in combination, as depicted in FIG. 7D: a method of highlighting the character corresponding to the numerical value of the split or the pitch displayed on the display section 131 of the interface device 100 or highlighting a corresponding specific message, and a method of letting the background portion of the display section 131 glow in red, and quickly blinking the numerical value, the character information indicating the specific message, or the background portion of the display section 131.

Moreover, in addition to any one of these alerting operations, a method of emitting an alert sound from the acoustic section 132 or replaying an alert message, and a method of continuously vibrating the vibrating section 133 may be applied singly or in combination.

These alerting operations are performed continuously for a predetermined time based on a control program executed by the CPU 141.

On the other hand, when the pace flag and the pitch flag do not satisfy the condition of the judging processing (Step S141), the CPU 141 further judges whether the condition is satisfied where the read pitch flag indicates "−1" and the read pace flag does not indicate "−1" (Step S142).

When the pitch flag and the pace flag satisfy the condition of the judging processing (Step S142), the CPU 141 judges that the pitch of the user US at the current point of time is below the set numerical value range (does not satisfy the lower-limit value) and being decreased, and causes the output interface section 130 to perform a predetermined caution (warning) operation (Step S147).

Regarding the caution operation performed herein, as described as the caution display state in the analyzing method and the informing method described above, for example, the following methods can be applied singly or in combination, as depicted in FIG. 7C: a method of highlighting the character corresponding to the numerical value of the pitch displayed on the display section 131 of the interface device 100 or highlighting a corresponding specific message, and a method of letting the background portion of the display section 131 glow in yellow, and slowly blinking the numerical value, the character information indicating the specific message, or the background portion of the display section 131.

Moreover, in addition to any one of these caution operations, a method of emitting a caution sound from the acoustic section 132 or replaying a caution message, and a method of intermittently vibrating the vibrating section 133 may be applied singly or in combination.

These caution operations are performed continuously for a predetermined time based on a control program executed by the CPU 141.

On the other hand, when the pace flag and the pitch flag do not satisfy the condition of the judging processing (Step S142), the CPU 141 further judges whether the condition is satisfied where the read pitch flag indicates "1" and the read pace flag indicates "1" (Step S143).

When the pitch flag and the pace flag satisfy the condition of the judging processing (Step S143), the CPU 141 judges that both of the pitch and the pace of the user US at the current point of time are above the numerical value range (exceeds the upper-limit value) and being overpitch and overpace, and causes the output interface section 130 to perform a predetermined caution operation (Step S148).

Regarding the caution operation performed herein, as with the caution operation described above (Step S147), the following methods can be applied singly or in combination: a method of highlighting the character corresponding to the corresponding numerical value displayed on the display section 131 of the interface device 100 or highlighting a corresponding specific message, and a method of changing the glowing state of the character information and the background portion of the display section 131.

Moreover, in addition to any one of these caution operations, predetermined caution operations by the acoustic section 132 and the vibrating section 133 may be applied singly or in combination.

On the other hand, when the pace flag and the pitch flag do not satisfy the condition of the judging processing (Step S143), the CPU 141 further judges whether the condition is satisfied where the read pace flag indicates "1" (Step S144).

When the pace flag satisfies the condition of the judging processing (Step S144), the CPU 141 judges that the pace of the user US at the current point of time is above the numerical value range and is being overpace, and causes the output interface section 130 to perform a predetermined caution operation (Step S149), as with the caution operation described above (Step S147).

On the other hand, when the pace flag does not satisfy the condition of the judging processing (Step S144), the CPU 141 further judges whether the condition is satisfied where the read pace flag indicates "−1" (Step S145).

When the pace flag satisfies the condition of the judging processing (Step S145), the CPU 141 judges that the pace of the user US at the current point of time is below the numerical value range and being decreased, and causes the output interface section 130 to perform a predetermined caution operation (Step S150), as with the caution operation described above (Step S147).

On the other hand, when the pace flag does not satisfy the condition of the judging processing (Step S145), the CPU 141 judges that both of the pitch and the pace of the user US at the current point of time are each within the numerical value range and a favorable or normal state is being kept, and causes the output interface section 130 to perform a normal operation (Step S151).

In the normal operation to be performed therein, as described as the standard display state in the analyzing method and the informing method described above, character information indicating numerical values such as a split, a movement distance, and a pitch are displayed on the display section 131 of the interface device 100 in a standard (normal) display format, for example, as depicted in FIG. 1B. That is, unlike the alerting display and the caution display described above, display in which the background portion of the display section 131 glows in a specific alert color or caution color or blinks, display in which a character corresponding to a numerical value is highlighted, etc., are not performed. Moreover, neither alerting operation by the acoustic section 132 nor caution operation by the vibrating section 133 is performed.

As described above, in the present embodiment, from the sensor section 110 incorporated in the interface device 100 serving as the exercise supporting device, information about the pace, the pitch, and the stride is obtained as information indicating an exercise motion status (running status) of the user US, and analyzing processing of judging whether the information is being kept within the preset numerical value range is performed, whereby the exercise motion status and its problematic point of the user US at the current point of time can be judged.

Then, based on the analysis result, an informing operation is performed on the display section 131 provided on the interface device 100 according to the exercise motion status and its problematic point, whereby the user US can precisely ascertain his or her own exercise motion status and its problematic point.

Therefore, for example, in a marathon or running, a factor leading to a decrease in pace or a slowdown at a time ahead of the current point of time (for example, in the latter half of a race or training) or its predictor can be specified and recognized in advance. By making a motion while mitigating the problematic point (a self correction), excessive physical exhaustion can be suppressed and a better record can be produced throughout the entire race or training.

Second Embodiment

Next, a second embodiment of the exercise supporting device according to the present invention is described.

In the first embodiment described above, the sensor section 110, the input interface section 120, and the output interface section 130 are integrally incorporated into the single wristwatch-type interface device 100.

However, in the second embodiment, the sensor section and the input and output interface sections are provided in separate devices.

Figure 13A:
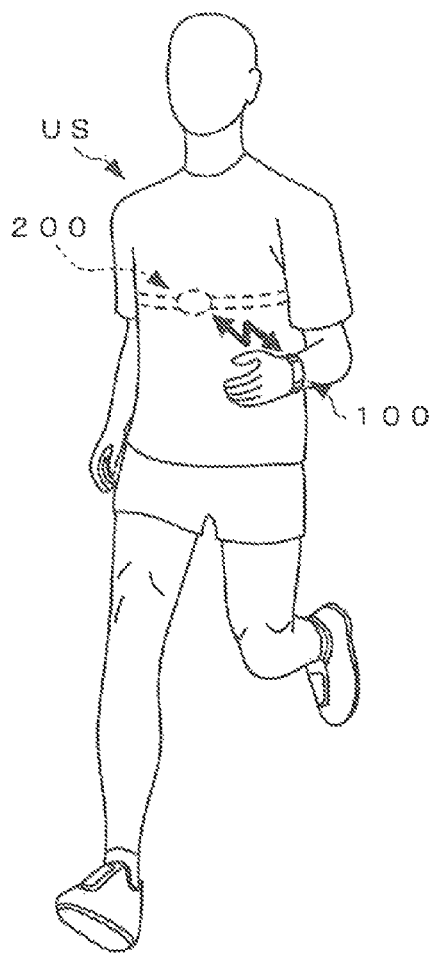
FIGS. 13A, 13B, and 13C are schematic structural diagrams showing an exercise supporting device of a second embodiment according to the present invention.
Figure 13B:
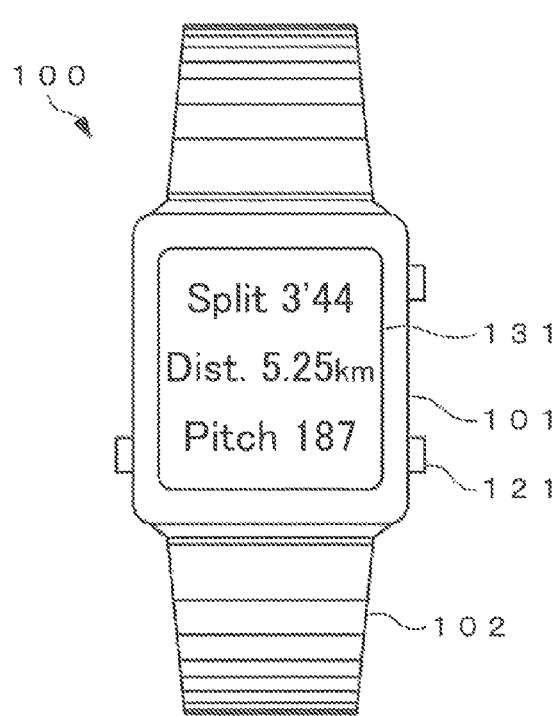
Figure 13C:
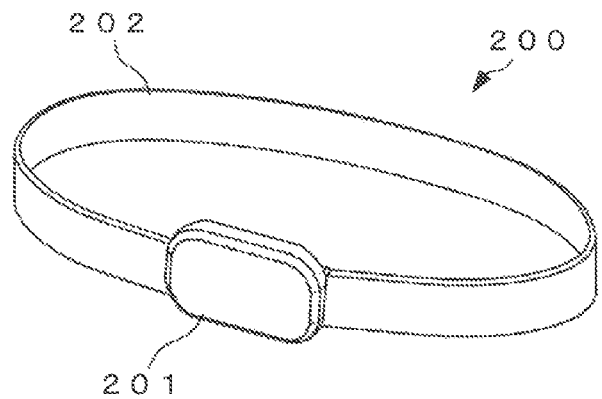

FIGS. 13A, 13B and 13C are schematic structural diagrams showing a second embodiment of the exercise supporting device according to the present invention.

Figure 14:
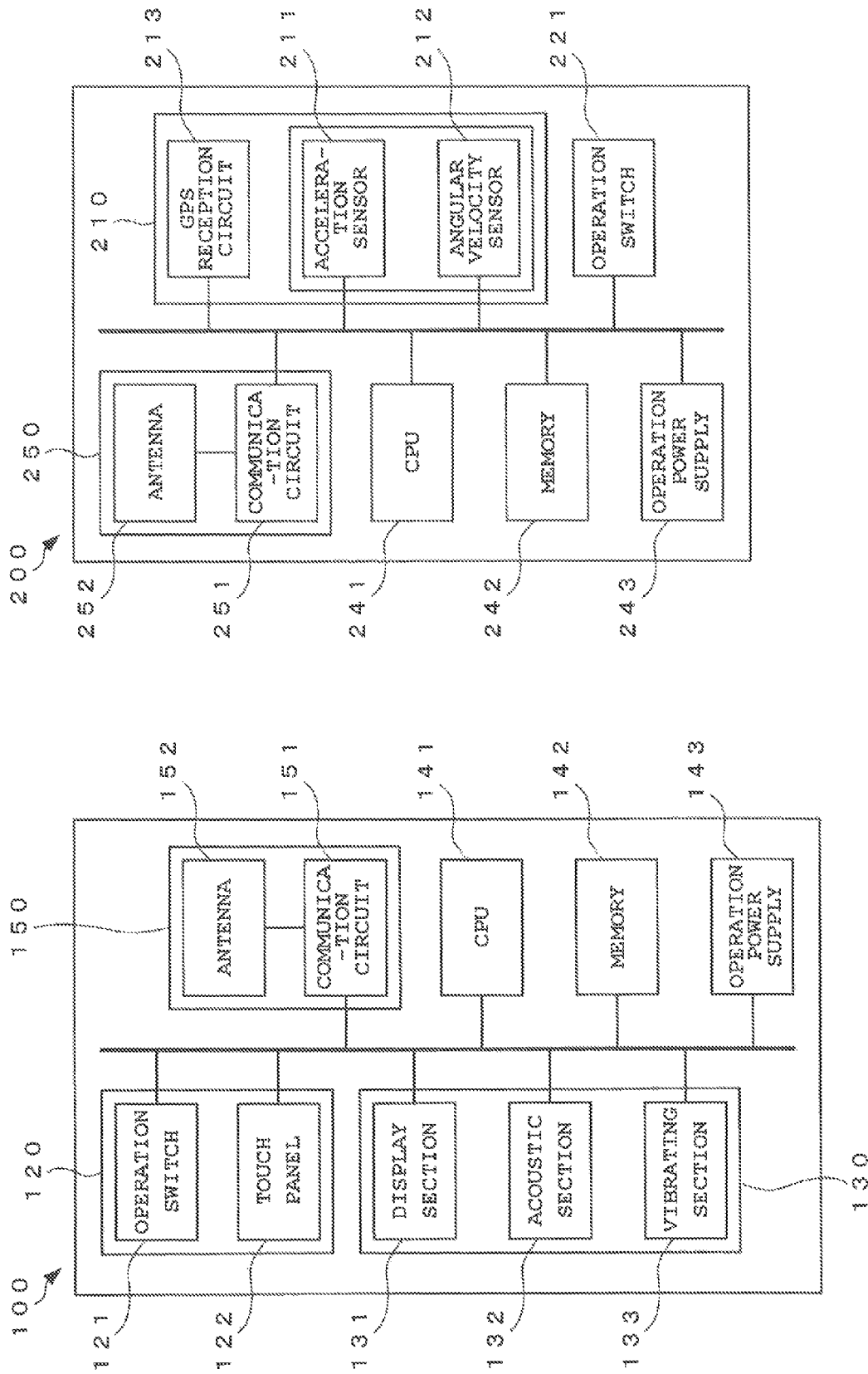
FIG. 14 is a block diagram showing an example of the structure of an interface device and a motion sensor that are applied to the exercise supporting device according to the second embodiment.

FIG. 14 is a block diagram showing an example of the structure of an interface device and a motion sensor that are applied to an exercise supporting device according to the second embodiment.

Here, components identical to those of the first embodiment are provided with the same reference numerals for convenience of explanation.

The exercise supporting device according to the second embodiment includes the interface device 100 that is worn on the wrist of the user US and a motion sensor section 200 that is worn on a chest part, as depicted in FIG. 13A to FIG. 13C.

Here, as with the first embodiment described above, the interface device 100 has an outer appearance of, for example, a wrist watch as depicted in FIG. 13B, and includes the device body 101 having the display section 131 and a belt section 102 for wearing the device body 101 on the wrist.

The motion sensor section 200 includes a device body 201 having a sensor section and a belt section 202 for wearing the device body 101 on the chest part such that it is wrapped around the chest part of the user US, as depicted in FIG. 13C.

The interface device 100 includes the input interface section 120, the output interface section 130, a communication function section 150, the CPU 141, the memory 142, and the operation power supply 143, as depicted in FIG. 14.

Here, the interface section 120, the output interface section 130, the CPU 141, the memory 142, and the operation power supply 143 each have a structure equivalent to that of a relevant component of the first embodiment described above.

The communication function section 150 includes, for example, a communication circuit 151 and an antenna 152, and transmits and receives various data to and from the motion sensor section 200 via wireless communications.

The motion sensor section 200 includes a sensor section 210, an operation switch 221, a communication function section 250, a CPU 241, a memory 242, and an operation power supply 243, as depicted in FIG. 14.

Here, the sensor section 210, the CPU 241, the memory 242, and the operation power supply 243 each have a structure equivalent to that of the sensor section 110, the CPU 141, the memory 142, and the operation power supply 143 depicted in the first embodiment described above. The operation switch 221 has, for example, a button switch or a slide switch. By operating the operation switch 221, for example, supply of the drive power (power-on) and cutting of the drive power (power-off) from the operation power supply 243 to each section inside the motion sensor section 200 and the start and stop of a sensing operation in the sensor section 210 are controlled. The communication function section 250 has, for example, a communication circuit 251 and an antenna 252, and transmits and receives various data to and from the above-described interface device 100 via wireless communications.

Here, regarding a data transmission method between the interface device 100 and the motion sensor section 200, Bluetooth (registered trademark) which is short-range wireless communication standards for digital devices, Bluetooth (registered trademark) low energy planned as a low-power consumption type in the communication standards, and the like can be favorably applied, as a wireless communication method.

As another transmission method applicable to the present embodiment, for example, a wired communication method via a communication cable can also be applied. In this case, the antenna 152 of the communication function section 150 of the interface device 100 and the antenna 252 of the communication function section 250 of the motion sensor section 200 can be omitted.

In the present embodiment as well, by performing an exercise supporting method similar to that of the above-described first embodiment, equivalent operations and effects can be obtained.

That is, in an example of the exercise supporting method in the present embodiment, various sensor data such as acceleration data and angular velocity data are obtained by the sensor section 210 incorporated in the motion sensor section 200, and are stored in the memory 242. Also, based on the sensor data, a pace, a pitch, and a stride are measured or calculated.

Then, the analyzing method and the informing method described in the above-described first embodiment are applied to these pace, pitch, and stride to judge an exercise motion status and its problematic point of the user US at the current point of time.

Analysis data (analysis result) indicating the judged exercise motion status and its problematic point is transmitted to the interface device 100 via the communication function section 250. The series of these operations is controlled by the CPU 241.

On the other hand, the interface device 100 stores the analysis data transmitted via the communication function section 150 in the memory 142. Also, by an informing method according to the judged exercise motion status and its problematic point, the user US is informed of exercise support information via the output interface section 130. The series of these operations is controlled by the CPU 141.

Also, in another example of the exercise supporting method in the present embodiment, various sensor data are obtained by the sensor section 210 incorporated in the motion sensor section 200, stored in the memory 242, and transmitted to the interface device 100 via the communication function section 250.

On the other hand, the interface device 100 stores the sensor data transmitted via the communication function section 150 in the memory 142, and also measures or calculates a pace, a pitch, and a stride based on the sensor data. By applying the analyzing method and the informing method described in the above-described first embodiment, the CPU 141 judges an exercise motion status and its problematic point of the user US at the current point of time.

Then, by an informing method according to the judged exercise motion status and its problematic point, the user US is informed of exercise support information via the output interface section 130.

By performing this exercise supporting method, as with the above-described first embodiment, the user US can precisely ascertain his or her own exercise motion status (running status) and its problematic point and, by making a motion while mitigating the problematic point, a better record can be produced throughout the entire race or training.

Also, in the present embodiment, the motion sensor section 200 including the sensor section 210 and the interface device 100 including the input interface section 120 and the output interface section 130 are structured as separate devices. Therefore, the sensor section 210 can be worn on any portion where an exercise motion status of the user US can be appropriately detected (sensed).

Therefore, accuracy of various sensor data detected by the sensor section 210 can be increased, and the user US can be informed of exercise support information based on a more accurate exercise motion status.

In the present embodiment, the motion sensor section 200 is a chest sensor type which is worn on the chest part of the user US. However, the present invention is not limited thereto.

That is, it is only required that the motion sensor section 200 is separated from an interface device including input and output interface sections. Also, the motion sensor section 200 may be worn on any body portion such as a leg, the waist, or the chest of the user in any form.

Here, when the motion sensor section 200 is a chest sensor type as described in the present embodiment, the sensor section 210 may further include a heartbeat sensor that detects the heartbeat of the user US during exercise motion.

In this case, a configuration may be adopted in which heartbeat data detected by the motion sensor section 200 is transmitted to the interface device 100 via the communication function section 250, stored in the memory 142, and displayed on the display section 131 as numerical value information of the heart rate at the current point of time.

Then, by applying the analyzing method and the informing method described in the exercise supporting method according to the first embodiment, when a heart rate out of a numerical value range set in advance is detected as in the case of the pace and the pitch, an alerting operation or a caution operation may be performed at the output interface section 130 of the interface device 100 to inform the user US of an anomaly.

Also, in each of the embodiments described above, the interface device 100 is a wrist watch type that is worn on a wrist. However, the present invention is not limited thereto.

That is, an electronic device having another structure may be worn on another part of the body as long as the electronic device can be worn on a part where the user can easily view or can view the numerical value information, the character information, etc. displayed on a display section included in the interface device.

For example, an electronic device including a display device, such as a portable phone or a smartphone, may be applied and worn on a wrist, an upper arm, etc. Alternatively, an electronic device including an eye-glasses-type display device may be applied.

Also, various sensor data and analysis data stored in the memory 142 of the interface device 100 and the memory 242 of the motion sensor section 200 in the exercise supporting device described in each of the embodiments may be transmittable to an external electronic device such as a personal computer, a portable phone, a smartphone, or a tablet terminal by a wireless or wired communication method or via a memory card or the like after the end of exercise motion.

By this configuration, for example, in the analyzing method described above, the analysis results (FIG. 6A and FIG. 6B) applied to the series of processing can be displayed and viewed on the display device provided to the external electronic device. Therefore, the exercise motion status and its problematic point in the race or training can be rechecked or analyzed in detail to be effectively utilized in the next and subsequent races and training.

Moreover, in each of the embodiments described above, as an example of exercise to which the exercise supporting device and the exercise supporting method according to the present invention are applied, the user participates in a marathon race or performs training such as running. However, the present invention is not limited thereto.

For example, the present invention may be applied to cases where the user participates in a race such as walking or performs exercises for its training.

While the present invention has been described with reference to the preferred embodiments, it is intended that the invention be not limited by any of the details of the description therein but includes all the embodiments which fall within the scope of the appended claims.

The invention claimed is:

1. An exercise supporting device comprising:
a detecting section which repeatedly detects motion data related to an exercise motion status of a user who is making an exercise motion by a moving motion;
an analyzing and judging section which obtains, based on the detected motion data, a movement distance from a moving motion start point of the user, a first motion information value corresponding to a moving speed of the user and a second motion information value corresponding to a footstep count of the user per unit time or a footstep width of the user, at each time the detecting section detects the motion data, wherein a plurality of movement distance ranges respectively corresponding to different movement distances have a plurality of respective first numerical value ranges in each of which a plurality of values are set as an allowable range of the first motion information value and a plurality of respective second numerical value ranges in each of which a plurality of values are set as an allowable range of the second motion information value, wherein the analyzing and judging section judges whether or not the first motion information value is out of a specific first numerical value range set for a specific movement distance range in which the movement distance when the first motion information value is obtained is included from among the plurality of first numerical value ranges, at each time the first motion information value is obtained, and wherein the analyzing and judging section judges whether or not the second motion information value is out of a specific second numerical value range set for the specific movement distance range from among the plurality of second numerical value ranges, at each time the second motion information value is obtained; and an output section which, when at least one of the first motion information value and the second motion information value is judged by the analyzing and judging section as being out of a relevant one of the specific first numerical value range and the specific second numerical value range, performs an informing operation regarding the first motion information value or the second motion information value judged as being out of the relevant one of the specific first numerical value range and the specific second numerical value range, during the exercise motion of the user, wherein the output section includes a display section which displays an image including character information, and wherein the output section:
performs, as the informing operation, a standard display on the display section with a first display format in which a display color of a background portion of the display section is set to a first background color, and character information included in a first image corresponding to the first motion information value and the second motion information value is displayed on the display section with a first size, when the analyzing and judging section judges that the first motion information value is within the specific first numerical value range and the second motion information value is within the specific second numerical value range;

performs, as the informing operation, a caution display on the display section with a second display format which is different from the first display format and in which the display color of the background portion of the display section is set to a second background color different from the first background color, and character information included in a second image corresponding to one of the first motion information value and the second motion information value is displayed on the display section with a second size larger than the first size, when the analyzing and judging section judges that only said one of the first motion information value and the second motion information value is out of a relevant one of the specific first numerical value range and the specific second numerical value range; and performs, as the informing operation, an alert display on the display section with a third display format which is different from the first display format and the second display format and in which the display color of the background portion of the display section is set to a third background color different from the first background color and the second background color, and character information included in a third image corresponding to the first motion information value and the second motion information value is displayed on the display section with a third size larger than the first size, when the analyzing and judging section judges that the first motion information value is out of the specific first numerical value range and the second motion information value is out of the specific second numerical value range.

2. The exercise supporting device according to claim 1, wherein the output section:
displays, on the display section in the first display format in the standard display, the character information included in the first image in a first character color;
displays, on the display section in the second display format in the caution display, the character information included in the second image at least one of in a second character color different from the first character color, and such that the character information blinks at a first time interval; and
displays, on the display section in the third display format in the alert display, the character information included in the third image at least one of in a third character color different from the first character color, and such that the character information blinks at a second time interval different from the first time interval.

3. The exercise supporting device according to claim 2, wherein the plurality of first numerical value ranges and the plurality of second numerical value ranges each have an upper-limit value and a lower-limit value, and
wherein the output section, in the second display format in the caution display, displays the character information included in the second image in a color that differs between when the analyzing and judging section judges that said one of the first motion information value and the second motion information value is larger than the upper-limit value of a relevant one of the specific first numerical value range and the specific second numerical value range, and when the analyzing and judging section judges that said one of the first motion information value and the second motion information value is smaller than the lower-limit value of a relevant one of the specific first numerical value range and the specific second numerical value range.

4. The exercise supporting device according to claim 3, wherein the output section, in the third display format in the alert display, sets the character information corresponding to the first motion information value in a color that differs between when the analyzing and judging section judges that the first motion information value is larger than the upper-limit value of the specific first numerical value range, and when the analyzing and judging section judges that the first motion information value is smaller than the lower-limit value of the specific first numerical value range; and
displays the character information included in the third image in a color that differs between when the analyzing and judging section judges that the second motion information value is larger than the upper-limit value of the specific second numerical value range, and when the analyzing and judging section judges that the second motion information value is smaller than the lower-limit value of the specific second numerical value range.

5. The exercise supporting device according to claim 2, wherein the character information in the second image includes text for instructing the user to adjust the moving speed to a value within the specific first numerical value range when the analyzing and judging section judges that the first motion information value is out of the specific first numerical value range; and includes text for instructing the user to adjust the footstep count to a value within the specific second numerical value range when the analyzing and judging section judges that the second motion information value is out of the specific second numerical value range, and
wherein the character information in the third image includes text for instructing the user to adjust the moving speed to a value within the specific first numerical value range and to adjust the footstep count to a value within the specific second numerical value range.

6. The exercise supporting device according to claim 1, wherein the character information in the second image includes a character indicating a numerical value of the moving speed of the user when the analyzing and judging section judges that the first motion information value is out of the specific first numerical value range; and includes a character indicating a numerical value of the footstep count of the user when the analyzing and judging section judges that the second motion information value is out of the specific second numerical value range, and
wherein the character information in the third image includes characters indicating the numerical value of the moving speed of the user and the numerical value of the footstep count of the user.

7. The exercise supporting device according to claim 1, wherein the output section:
displays in the second display format in the caution display, the background portion of the display section such that the background portion blinks at a third time interval; and
displays, in the third display format in the alert display, the background portion of the display section such that the background portion blinks at a fourth time interval different from the third time interval.

8. The exercise supporting device according to claim 1, wherein the output section further includes an acoustic section which emits a sound, and
wherein the output section causes the acoustic section to emit a caution sound constituted by a first sound as the informing operation, when the analyzing and judging section judges that said one of the first motion information value and the second motion information value is out of a relevant one of the specific first numerical value range and the specific second numerical value range; and
wherein the output section causes the acoustic section to emit an alert sound constituted by a second sound different from the first sound as the informing operation, when the analyzing and judging section judges that the first motion information value is out of the specific first numerical value range and the second motion information value is out of the specific second numerical value range.

9. The exercise supporting device according to claim 1, wherein the output section further includes a vibrating section which generates vibrations,
wherein the output section causes the vibrating section to generate vibrations with a first vibration pattern as the informing operation, when the analyzing and judging section judges that said one of the first motion information value and the second motion information value is out of a relevant one of the specific first numerical value range and the specific second numerical value range; and wherein the output section causes the vibrating section to generate vibrations with a second vibration pattern different from the first vibration pattern as the informing operation, when the analyzing and judging section judges that the first motion information value is out of the specific first numerical value range and the specific second motion information value is out of the second numerical value range.

10. The exercise supporting device according to claim 1, wherein the detecting section includes an acceleration sensor which detects a change ratio of the moving speed of the user as the motion data, and an angular velocity sensor which detects a change in a moving direction of the user as the motion data.

11. The exercise supporting device according to claim 10, wherein the detecting section further includes a position sensor which detects a geographical position of the user and the moving speed of the user as the motion data.

12. An exercise supporting method comprising:

repeatedly detecting motion data related to an exercise motion status of a user who is making an exercise motion by a moving motion;

obtaining, based on the detected motion data, a movement distance from a moving motion start point of the user, a first motion information value corresponding to a moving speed of the user and a second motion information value corresponding to a footstep count of the user per unit time or a footstep width of the user, at each time the motion data is detected, wherein a plurality of movement distance ranges respectively corresponding to different movement distances have a plurality of respective first numerical value ranges in each of which a plurality of values are set as an allowable range of the first motion information value and a plurality of respective second numerical value ranges in each of which a plurality of values are set as an allowable range of the second motion information value;

judging whether or not the first motion information value is out of a specific first numerical value range set for a specific movement distance range in which the movement distance when the first motion information value is obtained is included from among the plurality of first numerical value ranges, at each time the first motion information value is obtained;

judging whether or not the second motion information value is out of a specific second numerical value range set for the specific movement distance range from among the plurality of second numerical value ranges, at each time the second motion information value is obtained; and when at least one of the first motion information value and the second motion information value is judged as being out of a relevant one of the specific first numerical value range and the specific second numerical value range, performing an informing operation regarding the first motion information value or the second motion information value judged as being out of the relevant one of the specific first numerical value range and the specific second numerical value range, during the exercise motion of the user, wherein, in the informing operation:

a standard display is performed on a display section with a first display format in which a display color of a background portion of the display section is set to a first background color, and character information included in a first image corresponding to the first motion information value and the second motion information value is displayed on the display section with a first size, when it is judged that the first motion information value is within the specific first numerical value range and the second motion information value is within the specific second numerical value range;

a caution display is performed on the display section with a second display format which is different from the first display format and in which the display color of the background portion of the display section is set to a second background color different from the first background color, and character information included in a second image corresponding to one of the first motion information value and the second motion information value is displayed on the display section with a second size larger than the first size, when it is judged that only said one of the first motion information value and the second motion information value is out of a relevant one of the specific first numerical value range and the specific second numerical value range; and an alert display is performed on the display section with a third display format which is different from the first display format and the second display format and in which the display color of the background portion of the display section is set to a third background color different from the first background color and the second background color, and character information included in a third image corresponding to the first motion information value and the second motion information value is displayed on the display section with a third size larger than the first size, when it is judged that the first motion information value is out of the specific first numerical value range and the second motion information value is out of the specific second numerical value range.

13. The exercise supporting method according to claim 12, wherein the character information included in the first image is displayed on the display section in a first character color, in the first display format in the standard display, wherein the character information included in the second image is displayed on the display section at least one of in a second character color different from the first character color, and such that the character information blinks at a first time interval, in the second display format in the caution display, and wherein the character information included in the third image is displayed on the display section at least one of in a third character color different from the first character color, and such that the character information blinks at a second time interval different from the first time interval, in the third display format in the alert display.

14. A non-transitory computer-readable storage medium having stored thereon an exercise supporting program that is executable by a computer, the program being executable by the computer to perform functions comprising:

repeatedly detecting motion data related to an exercise motion status of a user who is making an exercise motion by a moving motion;

obtaining, based on the detected motion data, a movement distance from a moving motion start point of the user, a first motion information value corresponding to a moving speed of the user and a second motion information value corresponding to a footstep count of the user per unit time or a footstep width of the user, at each time the motion data is detected, wherein a plurality of movement distance ranges respectively corresponding to different movement distances have a plurality of respective first numerical value ranges in each of which a plurality of values are set as an allowable range of the first motion information value and a plurality of respective second numerical value ranges in each of which a plurality of values are set as an allowable range of the second motion information value;

judging whether or not the first motion information value is out of a specific first numerical value range set for a specific movement distance range in which the movement distance when the first motion information value is obtained is included from among the plurality of first numerical value ranges, at each time the first motion information value is obtained;

judging whether or not the second motion information value is out of a specific second numerical value range set for the specific movement distance range from among the plurality of second numerical value ranges, at each time the second motion information value is obtained; and when at least one of the first motion information value and the second motion information value is judged as being out of a relevant one of the specific first numerical value range and the specific second numerical value range, performing an informing operation regarding the first motion information value or the second motion information value judged as being out of the relevant one of the specific first numerical value range and the specific second numerical value range, during the exercise motion of the user, wherein, in the informing operation:

a standard display is performed on a display section with a first display format in which a display color of a background portion of the display section is set to a first background color, and character information included in a first image corresponding to the first motion information value and the second motion information value is displayed on the display section with a first size, when it is judged that the first motion information value is within the specific first numerical value range and the second motion information value is within the specific second numerical value range;

a caution display is performed on the display section with a second display format which is different from the first display format and in which the display color of the background portion of the display section is set to a second background color different from the first background color, and character information included in a second image corresponding to one of the first motion information value and the second motion information value is displayed on the display section with a second size larger than the first size, when it is judged that only said one of the first motion information value and the second motion information value is out of a relevant one of the specific first numerical value range and the specific second numerical value range; and an alert display is performed on the display section with a third display format which is different from the first display format and the second display format and in which the display color of the background portion of the display section is set to a third background color different from the first background color and the second background color, and character information included in a third image corresponding to the first motion information value and the second motion information value is displayed on the display section with a third size larger than the first size, when it is judged that the first motion information value is out of the specific first numerical value range and the second motion information value is out of the specific second numerical value range.

* * * * *